United States Patent
Kiani et al.

(10) Patent No.: US 9,375,569 B2
(45) Date of Patent: Jun. 28, 2016

(54) CONTROLLER UNIT FOR A FUNCTIONAL ELECTRICAL STIMULATION (FES) ORTHOTIC SYSTEM

(71) Applicant: Ensilver Canada, Markham (CA)

(72) Inventors: Farsad Kiani, Richmond Hill (CA); Jinbiao Zheng, Scarborough (CA)

(73) Assignee: Ensilver Canada, Markham (CA)

( * ) Notice: Subject to any disclaimer, the term of this patent is extended or adjusted under 35 U.S.C. 154(b) by 0 days.

(21) Appl. No.: 14/505,705

(22) Filed: Oct. 3, 2014

(65) Prior Publication Data

US 2015/0100104 A1    Apr. 9, 2015

Related U.S. Application Data

(60) Provisional application No. 61/886,239, filed on Oct. 3, 2013.

(51) Int. Cl.
| | | |
|---|---|---|
| *A61N 1/36* | (2006.01) | |
| *A43B 7/00* | (2006.01) | |
| *A43B 7/20* | (2006.01) | |
| *A43B 3/00* | (2006.01) | |

(52) U.S. Cl.
CPC ............ *A61N 1/36003* (2013.01); *A43B 3/0015* (2013.01); *A43B 7/00* (2013.01); *A43B 7/20* (2013.01)

(58) Field of Classification Search
USPC .......................................................... 607/49
See application file for complete search history.

(56) References Cited

U.S. PATENT DOCUMENTS

| | | | |
|---|---|---|---|
| 5,014,705 A | 5/1991 | Graupe et al. | |
| 5,016,635 A | 5/1991 | Graupe | |
| 5,070,873 A | 12/1991 | Graupe et al. | |
| 5,092,329 A | 3/1992 | Graupe et al. | |
| 6,324,432 B1 | 11/2001 | Rigaux et al. | |
| 6,456,884 B1 | 9/2002 | Kenney | |

(Continued)

FOREIGN PATENT DOCUMENTS

| | | |
|---|---|---|
| CA | 2074532 A1 | 5/1992 |
| CA | 2794533 A1 | 5/2007 |

(Continued)

OTHER PUBLICATIONS

Co-pending U.S. Appl. No. 14/529,854, filed Oct. 31, 2014, entitled "Cuff Unit for a Functional Electrical Stimulation (FES) Orthotic System".

(Continued)

*Primary Examiner* — Carl H Layno
*Assistant Examiner* — Jon Eric C Morales
(74) *Attorney, Agent, or Firm* — Bereskin & Parr LLP/S.E.N.C.R.L., s.r.l.

(57) ABSTRACT

Various embodiments are described herein for a method and system for facilitating a gait of a user with a functional electrical stimulation (FES) orthotic system. In some described embodiments, the method includes receiving a foot orientation indicator for a foot of the user; receiving a body inclination indicator for the user; determining a motion state based on the foot orientation indicator and the body inclination indicator; and defining signal parameters for a stimulation signal based on at least the motion state. The motion state can indicate a movement status of the user and therefore, the stimulation signal can be applied to the user for facilitating the gait of the user.

29 Claims, 10 Drawing Sheets

(56) References Cited

U.S. PATENT DOCUMENTS

| | | |
|---|---|---|
| 7,147,667 B2 | 12/2006 | Bedard |
| 7,632,239 B2 | 12/2009 | Dar et al. |
| 7,660,636 B2 | 2/2010 | Castel et al. |
| 7,867,284 B2 | 1/2011 | Bedard |
| 7,899,556 B2 | 3/2011 | Nathan et al. |
| 7,949,403 B2 | 5/2011 | Palermo et al. |
| 8,057,486 B2 | 11/2011 | Hansen |
| 8,082,035 B2 | 12/2011 | Glukhovsky |
| D658,769 S | 5/2012 | Moser et al. |
| 8,167,640 B2 | 5/2012 | Ochoa et al. |
| 8,175,713 B1 | 5/2012 | Cywinski |
| 8,209,022 B2 | 6/2012 | Dar et al. |
| 8,209,036 B2 | 6/2012 | Nathan et al. |
| 8,332,029 B2 | 12/2012 | Glukhovsky et al. |
| 8,364,277 B2 | 1/2013 | Glukhovsky |
| 8,382,688 B2 | 2/2013 | Dar et al. |
| 8,463,390 B2 | 6/2013 | Muraoka |
| 2003/0125781 A1 | 7/2003 | Dohno |
| 2003/0195586 A1 | 10/2003 | Rigaux et al. |
| 2003/0195587 A1 | 10/2003 | Rigaux et al. |
| 2004/0122483 A1 | 6/2004 | Nathan et al. |
| 2005/0261609 A1 | 11/2005 | Collings et al. |
| 2009/0030344 A1 | 1/2009 | Moser et al. |
| 2009/0240313 A1 | 9/2009 | Buhlmann et al. |
| 2010/0042180 A1 | 2/2010 | Mueller et al. |
| 2010/0191316 A1 | 7/2010 | Buhlmann et al. |
| 2011/0093035 A1 | 4/2011 | Moser et al. |
| 2011/0125290 A1 | 5/2011 | Langlois |
| 2011/0137429 A1 | 6/2011 | Bedard |
| 2011/0152968 A1 | 6/2011 | Nathan et al. |
| 2011/0282412 A1 | 11/2011 | Glukhovsky et al. |
| 2012/0059298 A1 | 3/2012 | Hoffman et al. |
| 2012/0116478 A1 | 5/2012 | Buhlmann et al. |
| 2012/0203156 A1 | 8/2012 | Dar et al. |
| 2012/0330375 A1 | 12/2012 | Nathan et al. |
| 2012/0330394 A1 | 12/2012 | Dar et al. |
| 2012/0330395 A1 | 12/2012 | Dar et al. |
| 2013/0013041 A1 | 1/2013 | Glukhovsky et al. |
| 2014/0259799 A1* | 9/2014 | McDonnell et al. ............ 36/140 |
| 2015/0100105 A1* | 4/2015 | Kiani et al. .................... 607/49 |
| 2015/0100107 A1 | 4/2015 | Kiani et al. |

FOREIGN PATENT DOCUMENTS

| | | |
|---|---|---|
| CA | 2649663 A1 | 11/2007 |
| CA | 2663030 A1 | 4/2008 |
| CA | 2697381 A1 | 2/2009 |
| CA | 2727812 A1 | 12/2009 |
| CA | 2732751 A1 | 2/2010 |
| CA | 2780328 A1 | 6/2011 |
| CA | 2782677 A1 | 6/2011 |
| CN | 202078650 U | 12/2011 |
| DE | 60 2004 005 692 T2 | 12/2007 |
| EP | 1201266 A1 | 5/2002 |
| EP | 1435891 A4 | 4/2003 |
| EP | 1530493 A1 | 3/2004 |
| EP | 1819395 A2 | 6/2006 |
| EP | 1874398 A4 | 10/2006 |
| EP | 1874404 A2 | 10/2006 |
| EP | 2037804 A2 | 12/2007 |
| EP | 1095670 B1 | 5/2008 |
| EP | 2120801 A1 | 7/2008 |
| EP | 1531767 B1 | 10/2008 |
| EP | 1980224 A2 | 10/2008 |
| EP | 2152359 A2 | 12/2008 |
| EP | 2180918 A2 | 2/2009 |
| EP | 2194862 A1 | 3/2009 |
| EP | 2247249 A1 | 8/2009 |
| EP | 2252242 A1 | 8/2009 |
| EP | 2291220 A1 | 12/2009 |
| EP | 2320993 A1 | 2/2010 |
| EP | 2506918 A1 | 6/2011 |
| EP | 2506919 A1 | 6/2011 |
| EP | 2392381 A2 | 12/2011 |
| EP | 1531766 B1 | 1/2012 |
| EP | 2097851 B1 | 2/2012 |
| EP | 2012669 B1 | 3/2013 |
| EP | 2586489 A1 | 5/2013 |
| JP | 201275933 A | 4/2012 |
| KR | 10-2005-0042793 A | 5/2005 |
| KR | 10-2005-0058417 A | 6/2005 |
| KR | 10-2006-0100427 A | 9/2006 |
| KR | 10-2009-0025184 A | 3/2009 |
| WO | 9209328 A1 | 6/1992 |
| WO | 2005-122740 A3 | 12/2005 |
| WO | 2006-061804 A8 | 6/2006 |
| WO | 2006-113802 A2 | 10/2006 |
| WO | 2007-125534 A2 | 11/2007 |
| WO | 2008-043065 A2 | 4/2008 |
| WO | 2008-086629 A1 | 7/2008 |
| WO | 2009-021157 A1 | 2/2009 |
| WO | 2009-026588 A2 | 2/2009 |
| WO | 2009-038861 A1 | 3/2009 |
| WO | 2009-052134 A1 | 4/2009 |
| WO | 2009-052135 A1 | 4/2009 |
| WO | 2009-088563 A1 | 7/2009 |
| WO | 2009-137234 A2 | 11/2009 |
| WO | 2009-155436 A1 | 12/2009 |
| WO | 2009-158389 A1 | 12/2009 |
| WO | 2010-002517 A1 | 1/2010 |
| WO | 2010-017004 A1 | 2/2010 |
| WO | 2010-107648 A1 | 9/2010 |
| WO | 2011-068823 A1 | 6/2011 |
| WO | 2011-068849 A1 | 6/2011 |
| WO | 2013-001526 A2 | 6/2012 |
| WO | 2012-107921 A1 | 8/2012 |
| WO | 2012-150500 A1 | 11/2012 |

OTHER PUBLICATIONS

Bioness Inc., "Bioness LiveOn NESS H200 Wireless: User's Guide", 2011.

Bioness Inc., "Bioness LiveOn NESS L300Plus: User's Guide", 2011.

Bioness Inc., "Bioness LiveOn NESS L300: Clinician's Guide", 2010.

Innovative Neurotronics, "WalkAide System: User Manual", 2010.

* cited by examiner

CONTROLLER UNIT FOR A FUNCTIONAL ELECTRICAL STIMULATION (FES) ORTHOTIC SYSTEM

CROSS REFERENCE TO RELATED APPLICATIONS

This application claims the benefit of U.S. Provisional Patent Application No. 61/886,239, filed Oct. 3, 2013 the entire contents of which are hereby incorporated by reference.

FIELD

The embodiments described herein relate to a controller unit for a functional electrical stimulation (FES) orthotic system, and in particular, methods and systems for improving a gait of a user with the FES orthotic system.

BACKGROUND

Individuals suffering from a central nervous system injury, such as a stroke, a brain injury, multiple sclerosis, cerebral palsy or partial spinal cord injuries, or other medical conditions may have mobility problems due to that injury or medical condition. Functional electrical stimulation (FES) systems may assist those individuals address those mobility problems.

Existing FES systems provide electrical stimulation to muscles that may have been paralyzed or affected due to the central nervous system injury or other medical conditions. The electrical stimulation may facilitate motion in those affected muscles. In some cases, FES systems may also help reeducate muscle movement, retard atrophy of any affected muscles due to disuse, and maintain or increase a range of motion at nearby joints.

An example application of an FES system is to enhance ankle dorsiflexion for individuals experiencing foot drop. Foot drop is a gait abnormality that stems from a weakness in a foot, damage to a peroneal nerve, or paralysis of muscles in an anterior portion of a lower leg. Foot drop may be caused by various conditions, such as muscle or spinal nerve trauma, abnormal anatomy, toxins and disease. Individuals affected by foot drop are unable to lift their foot and toes during a swing phase of their gait thereby causing their toes to be caught by the ground and their foot to drag on the ground. The FES system can assist those individuals by sending electrical stimulation signals to the affected muscles during the swing phase of their gait in order to trigger movement in those muscles so that the foot is lifted and not dragged along the ground.

Although existing FES systems are generally portable, they tend to be bulky and therefore, cumbersome for users to carry around on a daily basis. Existing FES systems also tend to lack versatility in operation and offer limited functionality.

SUMMARY

In a broad aspect, at least one embodiment described herein provides a method of facilitating a gait of a user with a functional electrical stimulation (FES) orthotic system. The method comprises receiving a foot orientation indicator for a foot of the user, the foot orientation indicator corresponding to an angular position of the foot relative to a reference axis, the reference axis being a longitudinal axis of the user in an initial state; receiving a body inclination indicator for the user, the body inclination indicator corresponding to a body position relative to the reference axis; determining a motion state based on the foot orientation indicator and the body inclination indicator, the motion state indicating a movement status of the user; and defining signal parameters for a stimulation signal based on at least the motion state, the stimulation signal being applied to the user for facilitating the gait of the user.

In at least one embodiment, determining the motion state may further comprise receiving an acceleration indicator for the user; identifying the motion state is a fallen state when the acceleration indicator exceeds a drop acceleration threshold and the body inclination indicator exceeds a drop inclination threshold; and identifying the motion state is an active state when the acceleration indicator indicates that the user is not stationary and is less than the drop acceleration threshold.

In at least one embodiment, in response to determining the motion state is the fallen state, defining signal parameters may further comprise generating an end signal for terminating any existing stimulation signal.

In at least one embodiment, in response to determining the motion state is the fallen state, defining signal parameters for the stimulation signal may further comprise at least one of turning off the FES orthotic system; transmitting an emergency message to a remote system; transmitting the motion state to the remote system; and generating an alarm signal.

In at least one embodiment, the drop acceleration threshold may be within a range of 1.5 g to 2.5 g.

In at least one embodiment, the drop inclination threshold may be within a range of 30 to 60 degrees.

In at least one embodiment, the method may further comprise, in response to determining the motion state is the active state, determining a terrain change of an environment of the user based on the foot orientation indicator and the body inclination indicator.

In at least one embodiment, determining the terrain change may comprise: identifying the terrain change is an ascending change when each of the foot orientation indicator and the body inclination indicator exceeds an ascent threshold; and identifying the terrain change is a descending change when each of the foot orientation indicator and the body inclination indicator exceeds a descent threshold.

In at least one embodiment, defining signal parameters for the stimulation signal may further comprise varying at least one aspect of the stimulation signal. Furthermore, in at least one embodiment, the at least one aspect of the stimulation signal may comprise an intensity of the stimulation signal, a frequency of the stimulation signal and a duration of the stimulation signal.

In at least one embodiment, varying the at least one aspect of the stimulation signal may comprise increasing an intensity of the stimulation signal when the terrain change is the ascending change; and decreasing the intensity of the stimulation signal when the terrain change is the descending change.

In at least one embodiment, the ascent threshold may be within a range of 15 to 25 degrees in a backward direction relative to the reference axis.

In at least one embodiment, the descent threshold may be within a range of 15 to 25 degrees in a forward direction relative to the reference axis.

In at least one embodiment, the body inclination indicator may be associated with a body part of the user other than the foot.

In at least one embodiment, defining signal parameters for the stimulation signal may further comprise adjusting an aspect of the stimulation signal by a predetermined interval.

In another broad aspect, at least one embodiment described herein provides a functional electrical stimulation (FES) orthotic system for facilitating a gait of a user. The FES orthotic system comprises a controller unit comprising a controller processor and at least one sensor. The controller processor is configured to receive a foot orientation indicator for a foot of the user, the foot orientation indicator corresponding to an angular position of the foot relative to a reference axis, the reference axis being a longitudinal axis of the user in an initial state; receive, from the at least one sensor, a body inclination indicator for the user, the body inclination indicator corresponding to a body position relative to the reference axis; determine a motion state based on the foot orientation indicator and the body inclination indicator, the motion state indicating a movement status of the user; and define signal parameters for a stimulation signal based on at least the motion state, the stimulation signal being applied to the user to facilitate the gait of the user.

In at least one embodiment, the controller processor may be further configured to receive an acceleration indicator for the user; identify the motion state is a fallen state when the acceleration indicator exceeds a drop acceleration threshold and the body inclination indicator exceeds a drop inclination threshold; and identify the motion state is an active state when the acceleration indicator indicates that the user is not stationary and is less than the drop acceleration threshold.

In at least one embodiment, in response to the controller processor determining the motion state is the fallen state, the controller processor may be further configured to generate an end signal for terminating any existing stimulation signal.

In at least one embodiment, in response to the controller processor determining the motion state is the fallen state, the controller processor may be further configured to perform at least one of: turning off the FES system; transmitting an emergency message to a remote system; transmitting the motion state to the remote system; and generating an alarm signal.

In at least one embodiment, in response to the controller processor determining the motion state is the active state, the controller processor may be further configured to determine a terrain change of an environment of the user based on the foot orientation indicator and the body inclination indicator.

In at least one embodiment, the controller processor may be further configured to identify the terrain change is an ascending change when each of the foot orientation indicator and the body inclination indicator exceeds an ascent threshold; and identify the terrain change is a descending change when each of the foot orientation indicator and the body inclination indicator exceeds a descent threshold.

In at least one embodiment, the controller processor may be further configured to vary at least one aspect of the stimulation signal.

In at least one embodiment, the controller processor may be further configured to: increase an intensity of the stimulation signal when the terrain change is the ascending change; and decrease the intensity of the stimulation signal when the terrain change is the descending change.

In at least one embodiment, the controller processor may be further configured to adjust an aspect of the stimulation signal by a predetermined interval.

In another broad aspect, at least one embodiment described herein provides a computer readable medium comprising a plurality of instructions executable on a processor of a device for adapting the processor to implement a method of facilitating a gait of a user with a functional electrical stimulation (FES) orthotic system. The instructions comprise receiving a foot orientation indicator for a foot of the user, the foot orientation indicator corresponding to an angular position of the foot relative to a reference axis, the reference axis being a longitudinal axis of the user in an initial state; receiving a body inclination indicator for the user, the body inclination indicator corresponding to a body position relative to the reference axis; determining a motion state based on the foot orientation indicator and the body inclination indicator, the motion state indicating a movement status of the user; and defining signal parameters for a stimulation signal based on at least the motion state, the stimulation signal being applied to the user for facilitating the gait of the user.

In at least one embodiment, the computer readable medium may comprise instructions for performing any of the methods described in accordance with the teachings herein.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

DETAILED DESCRIPTION OF DRAWINGS

For a better understanding of the various embodiments described herein, and to show more clearly how these various embodiments may be carried into effect, reference will be made, by way of example, to the accompanying drawings which show at least one example embodiment, and in which.

Figure 1:
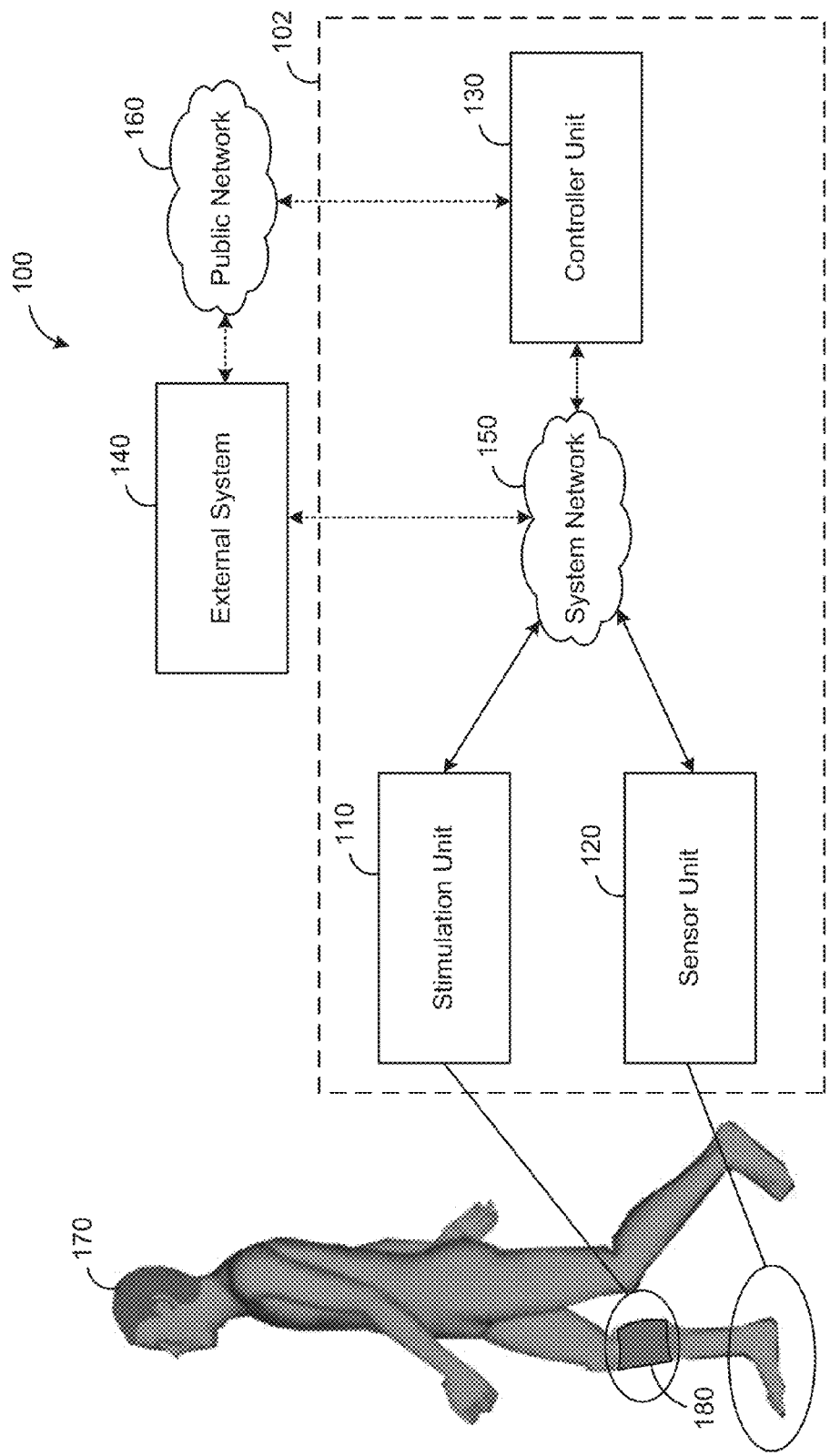
FIG. 1 is a block diagram of components interacting with a functional electrical stimulation (FES) system in accordance with an example embodiment.

Further aspects and advantages of the embodiments described herein will appear from the following description taken together with the accompanying drawing.

DESCRIPTION OF EXAMPLE EMBODIMENTS

The various embodiments described herein generally relate to methods (and associated systems configured to implement the methods) of facilitating a gait of a user with a functional electrical stimulation (FES) orthotic system. The gait is a manner of a user movement, such as how the user is walking or stepping. By receiving a foot orientation indicator for a foot of the user and a body inclination indicator for the user, the described system can determine a motion state that can assist user movement.

Both the foot orientation indicator and the body inclination indicator may be determined relative to a reference axis. The reference axis is a longitudinal axis of the user in an initial state of use of the FES system. The initial state may be when the user first initializes the FES system. The foot orientation indicator corresponds to an angular position of the foot relative to the reference axis. The angular position of the foot indicates how the foot is oriented with respect to the reference axis. The body inclination indicator corresponds to a body position as determined relative to the reference axis.

Based on the foot orientation indicator and the body inclination indicator, the described systems may determine the motion state so that appropriate signal parameters can be defined for a stimulation signal to be generated by the FES system.

Various apparatuses or processes will be described below to provide an example of an embodiment of the claimed subject matter. No embodiment described below limits any claimed subject matter and any claimed subject matter may cover processes or apparatuses that differ from those described below. The claimed subject matter is not limited to apparatuses or processes having all of the features of any one apparatus or process described below or to features common to multiple or all of the apparatuses or processes described below. It is possible that an apparatus or process described below is not an embodiment of any claimed subject matter. Any subject matter that is disclosed in an apparatus or process described below that is not claimed in this document may be the subject matter of another protective instrument, for example, a continuing patent application, and the applicants, inventors or owners do not intend to abandon, disclaim or dedicate to the public any such claimed subject matter by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures and components have not been described in detail so as not to obscure the example embodiments described herein. Also, the description is not to be considered as limiting the scope of the example embodiments described herein.

It should also be noted that the terms "coupled" or "coupling" as used herein can have several different meanings depending in the context in which these terms are used. For example, the terms coupled or coupling can have a mechanical or electrical connotation. For example, as used herein, the terms coupled or coupling can indicate that two elements or devices can be directly connected to one another or connected to one another through one or more intermediate elements or devices via an electrical element, electrical signal or a mechanical element depending on the particular context.

It should be noted that terms of degree such as "substantially", "about" and "approximately" as used herein mean a reasonable amount of deviation of the modified term such that the end result is not significantly changed. These terms of degree may also be construed as including a deviation of the modified term if this deviation would not negate the meaning of the term it modifies.

Furthermore, the recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed.

At least some of the elements of the systems described that are implemented via software may be written in a high-level procedural language such as object oriented programming or a scripting language. Accordingly, the program code may be written in C, C++, Java, SQL or any other suitable programming language and may comprise modules or classes, as is known to those skilled in object oriented programming. It should also be understood that at least some of the elements of the various systems described herein that are implemented via software may be written in assembly language, machine language or firmware as needed. In either case, the program code can be stored on a storage media or on a computer readable medium that is readable by a general or special purpose programmable computing device having a processor, an operating system and the associated hardware and software that is necessary to implement the functionality of at least one of the embodiments described herein. The program code, when read by the computing device, configures the computing device to operate in a new, specific and predefined manner in order to perform at least one of the methods described herein.

The computing devices that may be used in the various embodiments described herein generally include at least one processor, a data storage system (including volatile memory or non-volatile memory or other data storage elements or a combination thereof), and at least one communication interface. For example, and without limitation, the programmable devices (referred to herein as computing devices) may be a server, network appliance, an embedded device, a computer expansion module, a personal computer, a laptop, a personal data assistant, a cellular telephone, a smart-phone device, a tablet computer, a wireless device or any other computing device capable of being configured to carry out the methods described herein. The particular embodiment depends on the application of the computing device. For example, a server can be used to provide a centralized database and/or a remote programming interface while an embedded device may be used for components that are worn or otherwise directly used by the user.

In some embodiments, the communication interface may be a network communication interface. In embodiments in which elements are combined, the communication interface may be a software communication interface, such as those for inter-process communication (IPC). In still other embodiments, there may be a combination of communication interfaces implemented as hardware, software, and a combination thereof.

Program code may be applied to input data to perform at least some of the functions described herein and to generate output information. The output information may be applied to one or more output devices, in known fashion.

At least some of the programs may be implemented in a high level procedural or object oriented programming and/or scripting language, or both, to communicate with a computer system. However, other programs may be implemented in assembly or machine language, if desired. In any case, the language may be a compiled or interpreted language. The computer programs may be stored on a storage media or a device (e.g. ROM, magnetic disk, optical disc) readable by a general or special purpose programmable device, for configuring and operating the programmable device when the storage media or device is read by the programmable device to perform the procedures described herein. Embodiments of the system may also be considered to be implemented as a non-transitory computer-readable storage medium, configured with a computer program, where the storage medium so configured causes a computing device to operate in a specific and predefined manner to perform the functions described herein.

Furthermore, some of the programs associated with the system, processes and methods of the embodiments described herein are capable of being distributed in a computer program product comprising a computer readable medium that bears computer usable instructions for one or more processors. The medium may be provided in various forms, including non-transitory forms such as, but not limited to, one or more diskettes, compact disks, tapes, chips, and magnetic and electronic storage. In alternative embodiments the medium may be transitory in nature such as, but not limited to, wireline transmissions, satellite transmissions, internet transmissions (e.g. downloads), media, digital and analog signals, and the like. The computer useable instructions may also be in various formats, including compiled and non-compiled code.

Reference is first made to FIG. 1, which shows a block diagram 100 of components interacting with a functional electrical stimulation (FES) system 102 in accordance with an example embodiment. The FES system 102 generates stimulation signals to assist individuals, such as a user 170 of FIG. 1, with weakened, impaired or paralyzed muscles in a lower leg. The FES system 102 may generate stimulation signals for various purposes, such as to facilitate movement of the user 170, to reeducate any affected muscles in the user 170, to retrain the user 170 to walk, or to retard atrophy in muscles due to disuse, for example.

When facilitating movement of the user 170, the FES system 102 can generate stimulation signals to trigger movement at affected muscles. In the case of a user 170 with foot drop, for example, the FES system 102 may generate stimulation signals that are synchronized with a swing phase of a gait of that user 170 in order to help that user 170 lift the foot and prevent the foot from dragging on the ground.

As shown in FIG. 1, the FES system 102 includes a stimulation unit 110, a sensor unit 120 and a controller unit 130. The operation of the stimulation unit 110, the sensor unit 120 and the controller unit 130 will now be further described.

The stimulation unit 110, the sensor unit 120 and the controller unit 130 may communicate with each other via system network 150. As also shown in FIG. 1, the FES system 102 may also communicate with an external system 140 via the system network 150 and/or possibly via a public network 160. As will be described, the FES system 102 may receive signal parameters and other operational instructions from the external system 140 and may also transmit operational data to the external system 140.

Each of the stimulation unit 110, the sensor unit 120 and the controller unit 130 may include a real time calendar and clock (RTCC) component. The RTCC component may require a low frequency crystal or oscillator in order to operate. The RTCC component provides real time date and time information for the FES system 102. The date information may include the year, month, day and week, and the time information may include the hour, minute and second. The RTCC component may continue to operate even when the FES system 102 is in a sleep mode. Therefore, the RTCC component can facilitate system operations in which accurate time information is needed and with minimal power consumption. For example, the RTCC component can help ensure that a timer module at each of the stimulation unit 110, the sensor unit 120 and the controller unit 130 is synchronized so that stimulation signals are triggered at the appropriate time.

The FES system 102 may also enter into a safe mode in response to any communication errors between any two of the stimulation unit 110, the sensor unit 120 and the controller unit 130, as well as between the FES system 102 and the external system 140. For example, when the system network 150 fails to operate properly, the stimulation unit 110 may enter the safe mode and generate a predetermined safe stimulation signal for the user 170, no stimulation signal or provide a warning to the user 170 that a component of the FES system 102 is not functioning properly.

The stimulation unit 110 generates and delivers electrical stimulation signals to the user 170. As shown in FIG. 1, the stimulation unit 110 may be provided in association with a cuff 180 that is worn by the user 170 at a location on the user that is to receive the stimulation signals. In the example of FIG. 1, the cuff 180 is worn on the lower leg of the user 170 to stimulate nerves located in the lower leg. The stimulation unit 110 may include various modules for generating and delivering the stimulation signal to the user 170. It will be understood that the various modules may be hardware, software, and a combination of hardware and software. The stimulation unit 110 may be implemented in several ways as is known by those skilled in the art.

The stimulation unit 110 may generate stimulation signals based on signal parameters stored at the stimulation unit 110 or signal parameters received via the system network 150 from the external system 140 or the controller unit 130. The signal parameters received from the controller unit 130 may be determined based on a variety of factors, including an operational mode of the FES system 102 as selected by the user 170, data provided from waveform data charts and waveform parameters, and stimulation parameters as selected by the user 170 and a third party, such as a doctor or clinician. The signal parameters received from the external system 140 may include stimulation parameters as selected by the third party. In some embodiments, the stimulation unit 110 may vary amplitude or frequency of a stimulation signal based on the signal parameters.

In some embodiments, the stimulation unit 110 may generate multiple stimulation signals to different nerves of the user 170. By stimulating different nerves, different functionalities may be achieved by the FES system 102. The different stimulation signals may be generated at approximately the same time. For example, one to eight stimulation channels may be available at the stimulation unit 110 for generating up to eight stimulation signals. Each stimulation channel may be used for stimulating a different nerve, for example.

To deliver the stimulation signal, the stimulation unit 110 includes at least one electrode that is positioned substantially around a target muscle or a target nerve that is to receive the stimulation signal.

The stimulation unit 110 may also generate operation data, such as stimulation status data, to be displayed at the cuff 180 or by the controller unit 130. For example, the stimulation unit 110 may include a display component, such as an LCD display in some cases.

The sensor unit 120 includes multiple different sensors for detecting data associated with a gait of the user 170 and an environment of the user 170. As shown in FIG. 1, similar to the stimulation unit 110, the sensor unit 120 is generally worn by the user 170. In the example of FIG. 1, the sensor unit 120 is located at the foot of user 170. The sensor unit 120 may be attached to footwear worn by the user 170 or embedded into or otherwise attached to an insole of the user's footwear.

The sensor unit 120 may process at least a portion of the detected sensor data to generate various signal parameters for the stimulation signal. The sensor unit 120 may also transmit the detected sensor data to other components of the FES system 102, such as stimulation unit 110 and controller unit 130, and the external system 140. The detected sensor data may be transmitted in various data formats, such as in a hexadecimal byte format, for example.

Various sensors may be provided at the sensor unit 120. The sensors may include a force sensor, a temperature sensor, a gyroscope, an accelerometer, and a compass. Different embodiments may include all or different combinations of the aforementioned sensors.

The force sensor can detect an amount of force that it receives. For a sensor unit 120 that is located near or in the insole of the footwear of the user 170, the force sensor can detect the amount of force that is exerted by the foot of the user 170 while the user 170 walks. Based on data collected by the force sensor, the FES system 102 may distinguish between various movements of the user 170, such as whether that user 170 is standing, shifting their weight, is in mid-stride or is performing other activities.

The temperature sensor can detect a temperature of an environment of the user 170, for example.

The gyroscope can detect an angular velocity of the sensor unit 120 when the sensor unit 120 is in motion. Based on the detected angular velocity, the FES system 102 may determine an orientation of the sensor unit 120 and therefore an orientation of the foot of the user 170.

The accelerometer can detect an acceleration of the sensor unit 120.

The compass can detect a geomagnetic field of the sensor unit 120 to determine the direction in which the user 170 is walking.

The sensor unit 120 may also track a passage of time with a timer module, and transmit the time data via the system network 150. The sensor unit 120 may track the passage of time to facilitate data collection. For example, the sensor unit 120 may collect sensor data at predetermined time intervals, such as every 10 milliseconds, for example. A timer module may help to trigger data collection at the sensor unit 120. When the FES system 102 is used for addressing foot drop, the sensor unit 120 may track the passage of time to determine a lift period of the foot. The lift period is a period of time from when the user 170 lifts the foot from the ground to when that foot returns to the ground. The lift period may be used for generating the signal parameters for the stimulation signal.

The controller unit 130 can define the signal parameters of the stimulation signal and transmit the signal parameters to the stimulation unit 110 via the system network 150. The controller unit 130 may define the signal parameters based on data received from the sensor unit 120, the external system 140, or parameters stored locally or received at the controller unit 130.

The controller unit 130 is generally carried or worn by the user 170. The controller unit 130 may be a controller device, such as the controller device 200 shown in FIG. 2A, dedicated for use with the FES system 102. The controller device 200 may be attached to a waist of user 170, for example. The controller device 200 generally includes hardware and software modules for operating and interacting with each of the other units in the FES system 102 as well as external system 140. The controller device 200 may include one or more different user input controls for receiving input from the user 170, such as a mode button 210.

The controller unit 130 may also be provided as a controller software module that is installed onto existing computing devices that are carried by the user 170. The computing devices may include, but are not limited to, an electronic tablet device, a personal computer, a portable computer, a mobile device, a personal digital assistant, a laptop, a smart phone, a WAP phone, a handheld interactive television, handheld video display terminals, gaming consoles, and other portable electronic devices, for example. The controller software module may include one or more software modules for operating and interacting with each of the other units in the FES system 102 as well as the external system 140.

Figures 2A, 2B:
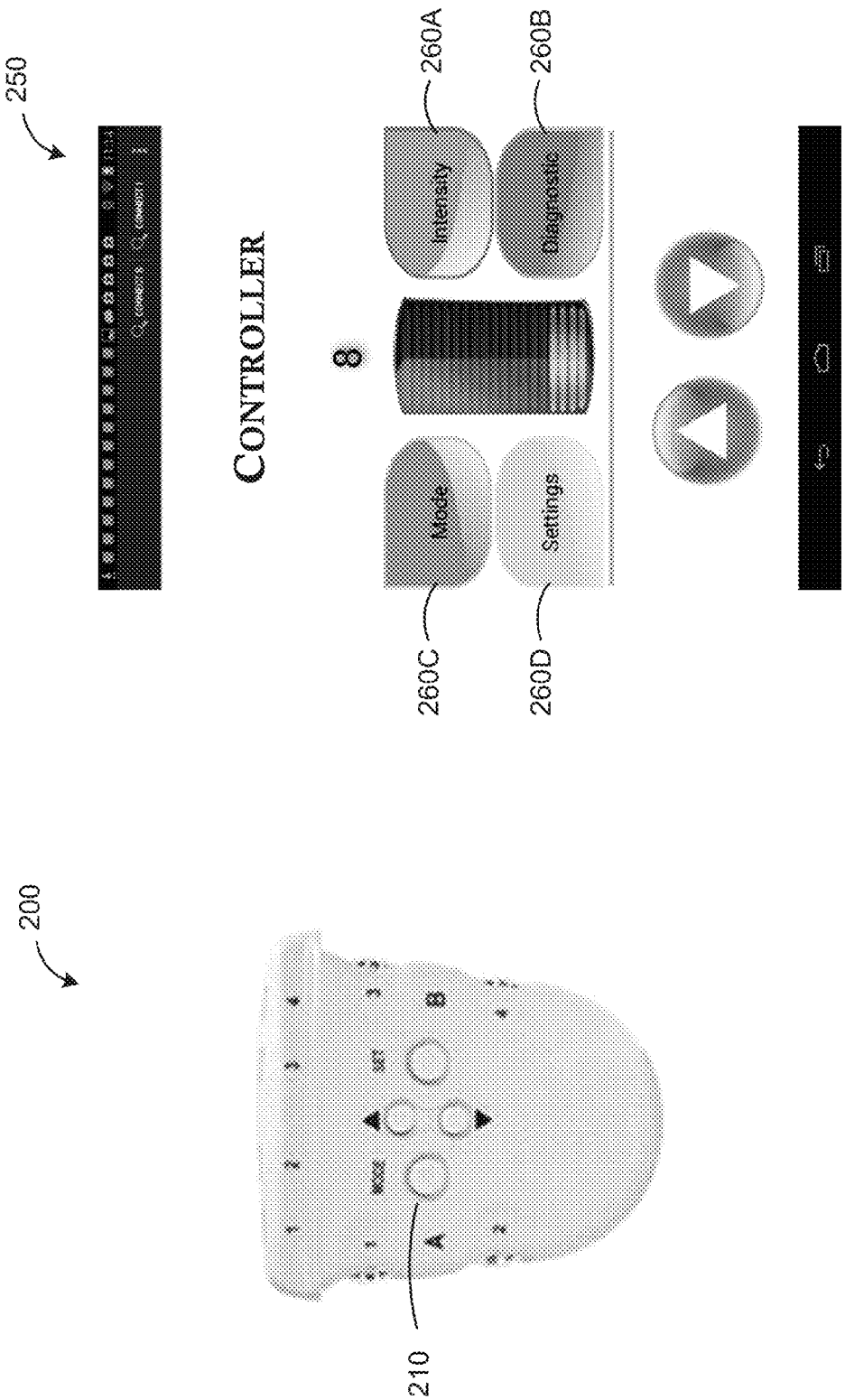
FIGS. 2A and 2B illustrate example embodiments of user interfaces for a controller unit of the FES system.

In at least some embodiments, the controller unit 130, whether provided as the controller device 200 or by another computing device, provides a user control interface from which to receive user inputs for operating the FES system 102. An example user control interface 250 for controller unit 130 is illustrated in FIG. 2B. The user control interface 250 includes more controls 260, such as an intensity control 260A, a diagnostic control 260B, a mode control 260C and a settings control 260D, with which user 170 can use for interacting with the FES system 102. It will be understood that the user control interface 250 may include more or fewer controls than shown in FIG. 2B, and that the controls may be different from those shown in FIG. 2B.

When the controller unit 130 receives a user input activating the intensity control 260A, the controller unit 130 may allow the user 170 to vary an intensity level of the stimulation signal. Similarly, when the controller unit 130 receives a user input activating the settings control 260D, the controller unit 130 may allow the user 170 to alter certain operation conditions of the FES system 102. The operation conditions that may be altered may vary based on user type. For example, the user 170 may be limited to cosmetic changes to the user control interface 250, such as background colour, but a doctor or clinician with access to the user control interface 250 may have increased access, such as to alter signal parameters.

In response to receiving a user input activating the mode control 260C, the controller unit 130 may enable the user 170 to change the operation mode of the FES system 102. Depending on the mode selected by the user 170, the controller unit 130 may vary the signal parameters accordingly.

As described, the FES system 102 may be used for different purposes, such as to facilitate movement of user 170, to reeducate any affected muscles, to retrain the user 170 to walk, or to retard atrophy of muscles due to disuse. Therefore, the FES system 102 may operate in different modes, such as a training mode, a walking mode, a test mode, and a sleep mode. The various different modes may be associated with stimulation signals having different intensity levels and frequencies. It will be understood that fewer or additional number of modes may be provided by the controller unit 130 in different embodiments.

The training mode may be used for reeducating affected muscles or to retard atrophy of muscles while the user 170 is sitting or lying down. The training mode may therefore be associated with stimulation signals that are not dependent on a movement of the user 170. Instead, the stimulation signals applied to the user 170 during the training mode can have a variety of intensities and frequencies. The training mode may also be used for initially fitting the user 170 with the stimulation unit 110.

The walking mode may be used for facilitating movement of the user 170. As a result, the walking mode may be associated with stimulation signals that are dependent on the movement of the user 170, unlike the stimulation signals associated with the training mode.

The test mode may be used for conducting functional tests and diagnostics of the FES system 102 in order to identify causes of any errors in the FES system 102. The test mode may also be used during calibration or repair of the FES system 102. For example, when the FES system 102 is in the test mode, the stimulation unit 110 may generate predefined stimulation signals at specific frequencies that can be identified for facilitating calibration.

The sleep mode can help the FES system 102 conserve power. Although each of the stimulation unit 110, the sensor unit 120 and the controller unit 130 may be equipped with a power supply, such as rechargeable lithium batteries for example, power saving can be important for extending a battery life of the FES system 102. Various different power states, such as a power down state, a low power state and an energy saving state may be used. For example, when the sleep mode is selected, the controller unit 130 may power down at least one of the stimulation unit 110 and the sensor unit 120, or place one of the stimulation unit 110 and the sensor unit 120 in a low power state or energy saving state.

In another example of when the sleep mode is selected, the controller unit 130 may synchronize a power usage state as between each of the stimulation unit 110, the sensor unit 120 and the controller unit 130. For synchronizing a low power state among the stimulation unit 110, the sensor unit 120 and the controller unit 130, the controller unit 130 may first transmit a low power state signal to the stimulation unit 110 via the system network 150. Once the stimulation unit 110 enters the low power state, the stimulation unit 110 may send a low power state signal to the sensor unit 120. After the sensor unit 120 enters the low power state, the sensor unit 120 may send a low power state signal to the controller unit 130. In response to receiving the low power state signal, the controller unit 130 transitions to a low power state. The power consumption of the FES system 102 during a low power state can be a nominal amount.

Each of the stimulation unit 110, the sensor unit 120 and the controller unit 130 can exit the sleep mode in response to receipt of an interrupt signal. The interrupt signal may be a user input received by the controller unit 130 for changing the operation mode from sleep mode, a physical movement of the user 170 as detected by the sensor unit 120, such as detection of a pressure change by the force sensor, or a user input received by the stimulation unit 110.

Still referring to FIG. 2B, when the controller unit 130 receives a user input indicating that the diagnostic control 260B has been selected, the controller unit 130 may prepare reports based on data associated with the operation of the FES system 102. The data associated with the operation of the FES system 102 may be stored with at least one of the controller unit 130 and remotely at external system 140.

The reports may be statistical reports or various usage reports. The operation data may include any data received from the sensor unit 120 and external system 140, and any data collected by the controller unit 130, such as error logs, usage logs, previous waveform parameters, and current waveform parameters. The usage logs may include time and date data, length of use, distance covered, speed, location data (e.g., data provided from the Global Positioning System (GPS)) and other related data.

Figure 3B:
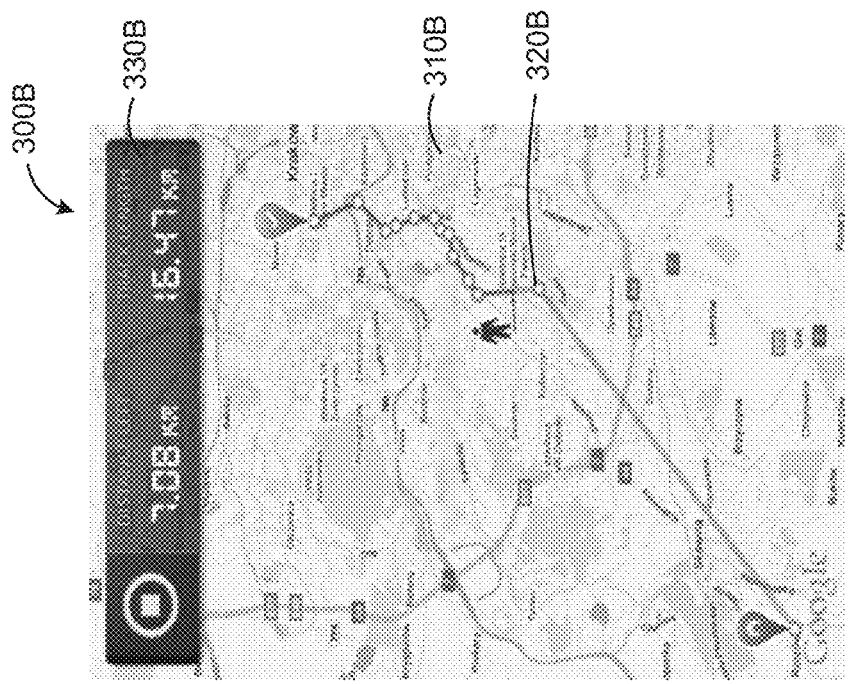
FIGS. 3A and 3B are example screenshots of usage reports generated by the controller unit of the FES system.
Figure 3A:
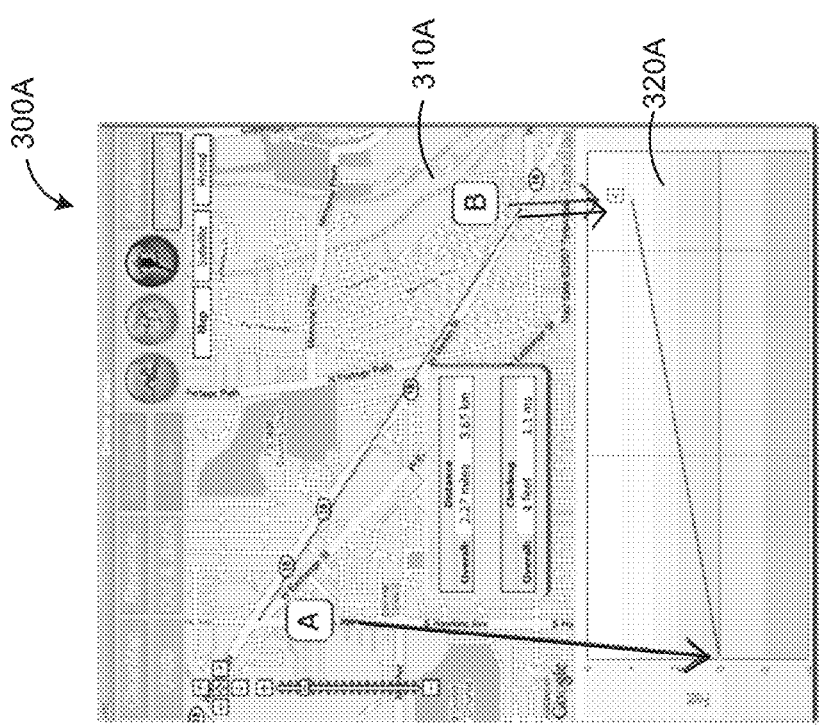

Reference is now made to FIGS. 3A and 3B, which are example usage reports 300A and 300B, respectively, generated by the controller unit 130.

The usage report 300A illustrates a workout performance report. The controller unit 130 may generate a map 310A illustrating a route covered by the user 170 during the workout as well as a progress display 320A illustrating a progress of the user 170. The controller unit 130 may additionally provide other performance evaluations, such as the amount of calories burned during the workout. Similarly, the usage report 300B is also a workout performance report. The usage report 300B includes a map 310B of the route of the user 170, a progress display 320B illustrating the progress of the user 170, and a usage summary 330B. For example, the progress display 320B can represent a speed of the user 170 by varying segments of the route based on the speed of the user 170 during that segment. If the user 170 is moving at a first speed during a first segment of the route, that first segment can be shown in the progress display 320B in a first colour or with a first pattern (e.g., solid line). If the user 170 then moves at a second speed that is different from the first speed during a second segment of the route, that second segment can be shown in the progress display 320B in a second colour that is different from the first colour or second pattern that is different from the first pattern (e.g., dotted line). Other manners of varying the display of the segments of the route may be used.

The reports generated by the controller unit 130 may be transmitted to the external system 140. Doctors, clinicians or other medical professionals who receive the reports via the external system 140 may review the reports and adjust the signal parameters accordingly.

Referring again to FIG. 1, the external system 140 may include any computing device with at least one processor and memory, and capable of receiving, sending, and processing instructions associated with the operation of the FES system 102. The external system 140 may be directly attached to the FES system 102, via a USB connection, or may connect remote with the FES system 102 as long as the external system 140 can communicate with the FES system 102 via the public network 160 or the system network 150.

It will be understood that although only one external system 140 is illustrated in FIG. 1, multiple external systems 140 may interact with the FES system 102 at one time. The number of external systems 140 that may interact with the FES system 102 at a given time may be limited by the data transmission capacity of the system network 150 and the public network 160.

The external system 140 may be an electronic tablet device, a personal computer, a workstation, a server, a portable computer, a mobile device, a personal digital assistant, a laptop, a smart phone, a WAP phone, an interactive television, video display terminals, gaming consoles and portable electronic devices or any combination of these.

Data associated with the usage of the FES system 102 by the user 170 may be transmitted to the external system 140 via the system network 150 or the public network 160. A third party, such as a doctor, clinician or other medical personnel, may access the external system 140 to retrieve the usage data. Based on the usage data, the third party may decide to vary and update certain signal parameters associated with the stimulation signal currently generated by the stimulation unit 110. The external system 140 may then transmit the updated signal parameters to the FES system 102 via the system network 150 or the public network 160.

The external system 140 may also include any device capable of measuring various physiological parameters, such as heart rate and blood oxygen levels. These devices may be worn or carried by the user 170 or attached to at least one unit of the FES system 102. Any physiological information received by the FES system 102 may be analyzed and used for adjusting signal parameters of the stimulation signals. For example, the physiological information may indicate that the heart rate of the user 170 exceeds a recommended heart rate threshold and the FES system 102 may respond by decreasing an intensity of the stimulation signal or even terminating the stimulation signal in order to minimize any risk of injury. The physiological information received by the FES system 102 may also be stored at the FES system 102 or at a remote storage system.

The system network 150 includes any network capable of carrying data between each of the stimulation unit 110, the sensor unit 120 and the controller unit 130, as well as between the FES system 102 and the external system 140. System network 150 may include one or more wireless communication networks, such as Wireless LAN (WLAN), a local area network implemented by using technologies such as, but not limited to Bluetooth™ technology or maybe infrared light (in certain cases), and other networks implemented using similar protocols and technologies. The system network 150 may also include multiple sub-networks.

Networks implemented using Bluetooth technologies may be Personal Area Networks (PAN) and can provide enhanced security in comparison with other wireless networks. It is well known that a Bluetooth communication network is capable of exchanging data between different devices over short distances using short-wavelength radio transmissions in the ISM radio band of 2,400 to 2,480 MHz.

Due to the multiple different units within the FES system 102 that may be required to communicate with each other, the FES system 102 may require multi-point connections. When the system network 150 is implemented with Bluetooth technology, the system network 150 may facilitate multi-point connections by entering a special command mode in which two different protocols are used. The two different protocols include the standard Bluetooth communication protocol and an FES system protocol that converts data provided in the standard Bluetooth communication protocol into data recognizable by each of the different units within the FES system 102.

In a command mode, any data received by system network 150 is first interpreted based on the standard Bluetooth communication protocol. Based on the standard Bluetooth communication protocol, the received data is processed and encapsulated with extra bytes in order to match data traditionally provided in the command mode. The processed data can then be interpreted using the FES system protocol.

In embodiments in which the system network 150 is implemented using Bluetooth technology, the FES system 102 may operate to minimize errors in data transmission caused by environmental factors.

The public network 160 can include any network capable of carrying data between the external system 140 and the FES system 102. Generally, the public network 160 may be any communication network that is used as the system network 150. However, unlike the system network 150, the public network 160 may also facilitate communication for the external system 140 when the external system 140 is outside of the range of the system network 150. For example, the public network 160 may include the Internet, Ethernet, a plain old telephone service (POTS) line, a public switch telephone network (PSTN), an integrated services digital network (ISDN), a digital subscriber line (DSL), coaxial cable, fiber optics, satellite, mobile, wireless (e.g. Wi-Fi, WiMAX), SS7 signaling network, fixed line, local area network, wide area network, and others, including any combination of these.

As described, controller unit 130 may be a dedicated controller device 200 for the FES system 102. The controller device 200 may have a display, such as a LCD display or a touch sensitive display. The controller device 200 is generally lightweight and may have a weight of approximately 70 g, for example. Alternatively, the controller unit 130 may be a computing device, such as smart phones, personal digital assistant devices, electronic tablet devices, or other similar devices.

Figure 4:
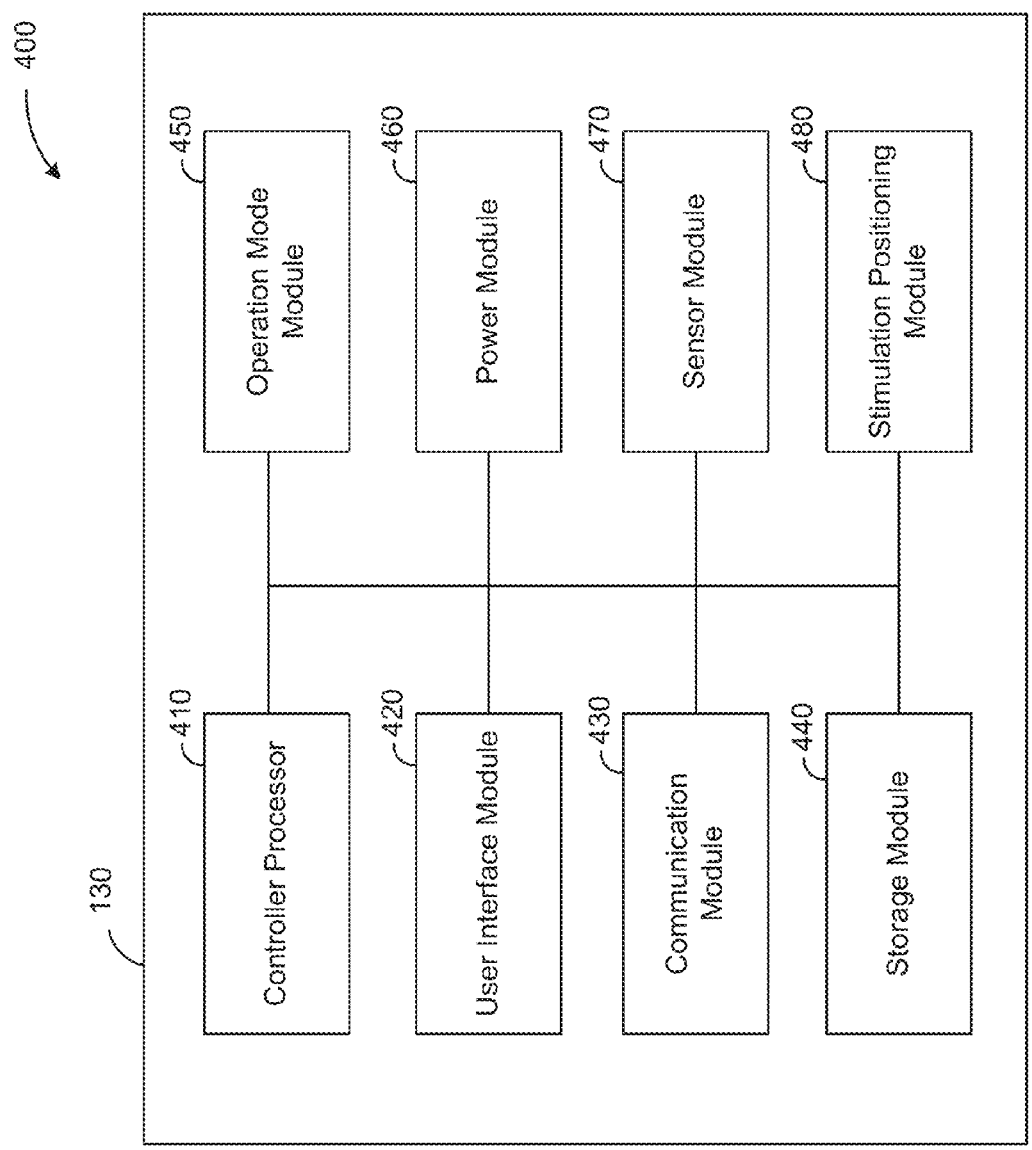
FIG. 4 illustrates a block diagram of an example embodiment of a controller unit of the FES system in accordance with the teachings herein.

Reference is now made to FIG. 4, which is a block diagram of an example embodiment of a controller unit 130. As shown in FIG. 4, the controller unit 130 includes a controller processor 410, a user interface module 420, a communication module 430, a storage module 440, an operation mode module 450, a power module 460, a sensor module 470 and a stimulation positioning module 480.

The controller processor 410 may implement the various methods described herein. The controller processor 410 may receive, via the communication module 430, in some embodiments, data from other components such as the stimulation unit 110, the sensor unit 120 or the external system 140. Based on at least the received data and data stored at the storage module 440, the controller processor 410 may generate usage reports, such as 300A and 300B. The controller processor 410 may also transmit data, such as signal parameters associated with a stimulation signal to be applied to the user 170 via the communication module 430. In another example, the controller processor 410 may operate with the operation mode module 450 to transition the FES system 102 into different operation modes based on inputs received via the user interface module 420.

The user interface module 420 can facilitate interaction between the user 170 and the controller unit 130. For example, the user interface module 420 can provide the user control interface 250 as described with reference to FIG. 2B. Other control interfaces may similarly be provided by the user interface module 420.

In some embodiments, the user interface module 420 can generate operation status information to be displayed to the user 170. When the controller unit 130 is provided as the controller device 200, the operation status information may be shown on a display provided on the controller device 200. Alternatively, when the controller unit 130 is provided on a computing device, such as a smart phone or tablet, the operation status information can be shown on the display of that computing device. The user interface module 420 can also receive inputs via user input controls such as, but not limited to, push buttons and text fields, for example.

Figure 5:
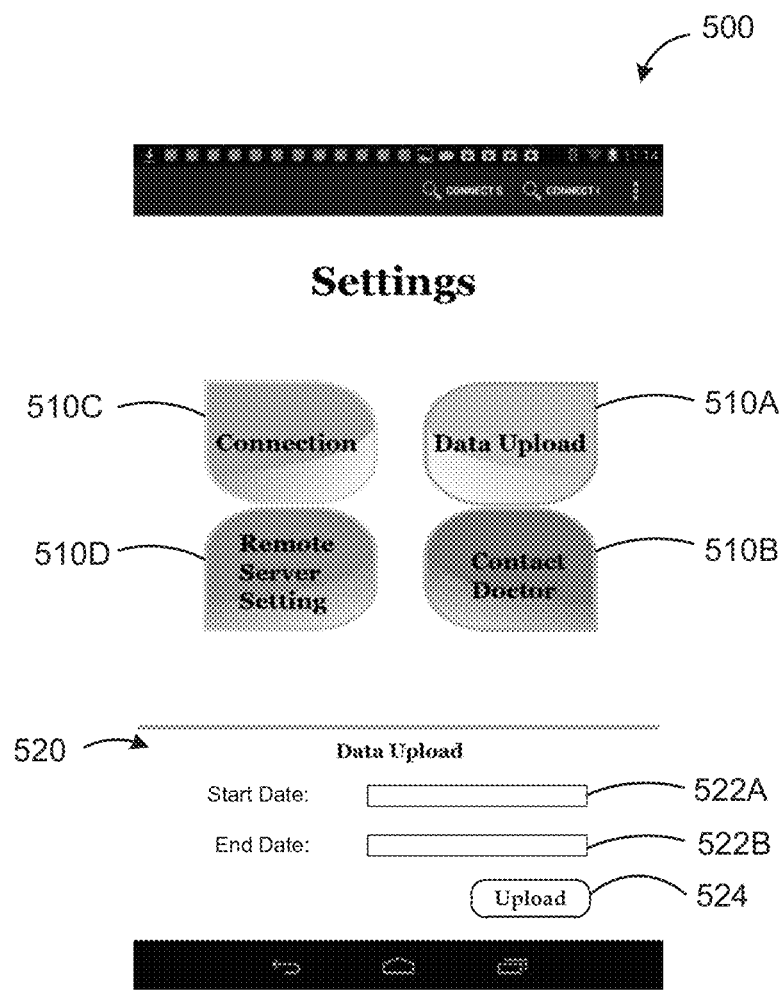
FIG. 5 illustrates another example embodiment of a user control interface for the controller unit of the FES system.

An example embodiment of another user control interface 500 is shown in FIG. 5. The user control interface 500 includes several different controls 510, such as a data upload control 510A, a contact doctor control 510B, a connection control 510C and a remote server control 510D.

When the user interface module 420 receives a user input activating the data upload control 510A, the controller processor 410 can be triggered to operate with the communication module 430 and the storage module 440 to transmit certain data stored at the storage module 440 to the external system 140.

In some embodiments, the user interface module 420 may generate a sub-control interface in response to detecting an activation of any of the controls 510 provided by the user control interface 500. For example, when the user interface module 420 detects that the data upload control 510A has been selected, the user interface module 420 may provide an upload sub-control interface 520. The upload sub-control interface 520 can receive inputs from the user 170 for defining parameters of the data to be transmitted to the external system 140. To facilitate the definition of data parameters, the upload sub-control interface 520 can include various user input fields 522 and user input controls, such as a start date field 522A, an end date field 522B and an upload button 524. With the start date field 522A and the end date field 522B, the user interface module 420 can receive a date range from the user 170 for defining the duration of data to be transmitted to the external system 140. Activation of the upload button 524 can confirm transmission of the defined range of data. It will be understood that other controls and fields may similarly be provided in the upload sub-control interface 520.

The controller processor 410 may operate with the communication module 430 to initialize an interaction with a third party, such as a medical professional, when the user interface module 420 receives an input selecting the contact doctor control 510B. For example, the controller processor 410 may initialize, via the communication module 430, an electronic message to be sent to or to be received from the third party. The user interface module 420 may receive an input activating the contact doctor control 510B when user 170 experiences problems with the FES system 102 or would like to contact a medical professional for adjusting the stimulation signals.

In some embodiments, in response to receiving the input selecting the contact doctor control 510B, the controller processor 410 can also transmit relevant data to the external system 140 or receive updates from the external system 140. For example, the controller processor 410 may trigger transmission of certain usage data and error logs to the external system 140. The controller processor 410 may also receive updated signal parameters from the medical professional via the external system 140.

Still referring to FIG. 5, when the user interface module 420 receives an input that activates the connection control 510C, the controller processor 410 can be triggered to generate a sub-control interface for user 170 to select a connection type for the FES system 102. For example, the connection type may be any communication implementation supported by the system network 150 or the public network 160, such as a Bluetooth connection, a Wi-Fi connection, a WLAN network or a cellular network.

When the user interface module 420 indicates that the remote server control 510D is activated, the user interface module 420 may present a sub-control interface for the user 170 to edit how the controller unit 130 interacts with the external system 140. For example, the user interface module 420 can enable the user 170 to set a frequency at which the controller unit 130 interacts with the external system 140 or to limit the type of external systems 140 that can interact with the controller unit 130.

It will be understood that the user control interface 500 is provided only for the purpose of exposition and that more or fewer user controls than shown in FIG. 5 may be used in various embodiments. It will be further understood that other types of user controls may be provided on the user control interface 500.

Referring again to FIG. 4, the communication module 430 can act as an interface between the controller unit 130 and components external to the controller unit 130. For example, the communication module 430 can enable interaction between the controller unit 130 and each of the stimulation unit 110 and the sensor unit 120 via the system network 150. The communication module 430 can also facilitate interaction between the controller unit 130 and the external system 140 via the system network 150 or the public network 160. As described, any interaction between the controller unit 130, the stimulation unit 110, the sensor unit 120 and the external system 140 can be based on any wireless communication, such as Bluetooth technology or other wireless communication protocols and technologies, such as WLAN.

The communication module 430 may include a GPS receiver for receiving data from satellites. The data received from the satellites may include location information (e.g., longitude and latitude) and time information (e.g., date and time). For example, the GPS receiver can determine a user location of the user 170. Based on the user location data received via the communication module 430, the controller processor 410 may determine a speed of the user 170 and generate the usage reports 330A, 300B accordingly.

In some embodiments, the communication module 430 may also include connection ports for facilitating transfer of data from the controller unit 130 to other components, such as the stimulation unit 110 and the external system 140. The connection ports may include a Universal Serial Bus (USB) interface.

The storage module 440 can store operation data received from the stimulation unit 110, the sensor unit 120, or the external system 140. For example, the operation data may include usage data and error logs. The usage data may include past and present signal parameters of the stimulation signal. The signal parameters may be defined by the third party via the external system 140 or by the FES system 102, such as by the controller processor 410.

The operation mode module 450 can facilitate transitions between the various operational modes described herein. As described with reference to FIG. 2B, the FES system 102 can support different modes, such as the training mode, the walking mode, the test mode and the sleep mode. The operation mode module 450 can configure the FES system 102 to enter an operation mode associated with an input received via the user interface module 420. The operation mode module 450 may be implemented as a software module that is executed by the controller processor 410.

In some embodiments, the operation mode module 450 can also provide signal parameters that are associated with each operational mode. For example, when the user input is associated with the training mode, the operation mode module 450 can provide signal parameters that correspond to the training mode. Similarly, when the user input is associated with the sleep mode, the operation mode module 450 can terminate signal parameters so that the FES system 102 can enter a low power state.

The power module 460 can include a power regulator for monitoring power consumption by the controller unit 130 and also by the FES system 102. With respect to the power consumption of the controller unit 130, the power regulator helps ensure that stable and reliable power is provided to the other modules of the controller unit 130. The power module 460 may also include a charge monitor for managing the current and voltage of the controller unit 130 when the controller unit 130 is being charged. In some embodiments, the power module 460 may operate with the communication module 430 for receiving power through the USB interface.

The power module 460 can also monitor power consumption at the stimulation unit 110 and the sensor unit 120. For example, when the power module 460 detects that a battery level of the stimulation unit 110 is low, the power module 460 can trigger the stimulation unit 110 to enter a low power state. To further reduce power consumption, the power module 460 may reduce the number of active electrodes and stimulation channels, depending on the particular embodiment of the FES system 102. The power module 460 may also generate a notification signal in response to detecting low battery levels at one of the stimulation unit 110 and the sensor unit 120.

In some embodiments, instead of using the power module 460 to monitor power consumption at each of the stimulation unit 110 and the sensor unit 120, each of the stimulation unit 110 and the sensor unit 120 can include a local power module for monitoring power consumption.

The power module 460 may also operate based on commands received from other modules in the controller unit 130. For example, the power module 460 may be triggered to exit the sleep mode in response to a wake-up signal received from the user interface module 420, such as when a wake-up button is activated or when any user input is received.

The sensor module 470 can include one or more sensors for detecting data associated with user movement and environmental data, such as an ambient temperature. The sensors may include an accelerometer and a gyroscope. Data associated with user movement can include user orientation, user position and an acceleration indicator. The acceleration indicator can include a rate at which a velocity of the user 170 changes with time and a normalized gravitational acceleration value (in multiples of the standard gravity). In some embodiments, the acceleration indicator can be associated with an upper body of the user 170.

The sensor module 470 can provide sensor data to the controller processor 410 which can be used for various purposes, such as determining the motion state. For example, as will be described, the controller processor 410 can determine that the user 170 is in a fallen state when the acceleration indicator and the body inclination indicator exceed a drop threshold. The controller processor 410 may also determine that the user 170 is in an active state when the acceleration indicator indicates the user 170 is not stationary. The controller processor 410 may determine the motion state based also on data provided by the sensor unit 120.

The stimulation positioning module 480 can assist with placement of the electrodes on the user 170. A flowchart 600 of an example embodiment of a method for positioning the electrodes by using the controller unit 130 is shown in FIG. 6.

Figure 6:
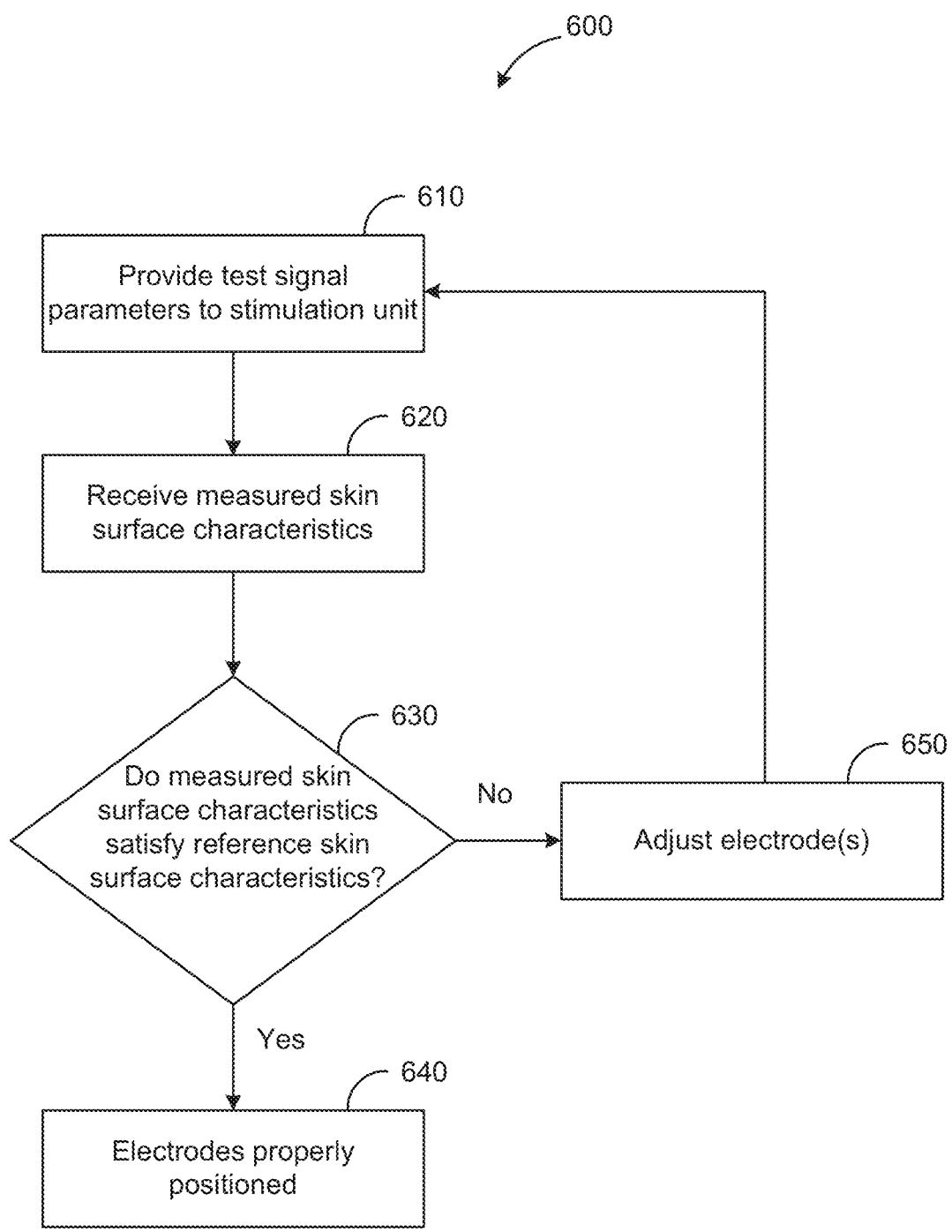
FIG. 6 is a flowchart of an example embodiment of a method for positioning electrodes with the controller unit of the FES system in accordance with the teachings herein.

With respect to FIG. 6, at 610, the controller processor 410 provides test signal parameters to the stimulation unit 110. The test signal parameters correspond to test stimulation signals that can assist with the placement of the electrodes at the stimulation unit 110.

Generally, when a stimulation signal is applied to the skin of the user 170 via the electrodes, the electrodes at the stimulation unit 110 can measure skin surface characteristics resulting from application of the stimulation signal. The skin surface characteristic may include a surface resistance. The surface resistance can vary due to different skin surface characteristics but will be generally be within approximately 5 kΩ to 25 kΩ for an average user. There is likely an error when the surface resistance is determined to be less than 1 kΩ (a short circuit error) or greater than 50 kΩ (an open circuit error).

The test signal parameters are associated with reference skin surface characteristics that correspond to a desired location for the placement of the electrodes. The test signal parameters may be default signal parameters defined by the manufacturer or customized for the user 170 by a third party.

At 620, the controller processor 410 receives measured skin surface characteristics resulting from application of the test stimulation signals. Electrodes at the stimulation unit 110 can measure a response current that is generated in response to the application of the test stimulation signal. The stimulation unit 110 can determine corresponding skin surface characteristics based on the response current and provide the determined skin surface characteristics to the controller unit 130. The measured skin surface characteristics may be stored in the storage module 440.

At 630, the controller processor 410 determines if the measured skin surface characteristics satisfy the reference skin surface characteristics. If the controller processor 410 determines that the measured skin surface characteristics satisfies the reference skin surface characteristics, the controller processor 410 can proceed to 640. However, if the controller processor 410 determines that the measured skin surface characteristics do not satisfy the reference skin surface characteristics, the controller processor 410 proceeds to 650.

For example, when the FES system 102 is fitted for the user 170, a user surface resistance may be determined specifically for that user 170 and stored in the storage module 440 as part of the reference skin surface characteristics. The electrodes at the stimulation unit 110 are properly positioned for that user 170 when the measured surface resistance corresponds to the user surface resistance or within a reasonable range of the user surface resistance.

At 640, the controller processor 410 can indicate that electrode(s) at the stimulation unit 110 are properly positioned. For example, the controller processor 410 can generate a success signal to notify the user 170 that the electrodes are properly positioned. The success signal may be a message indicating success that may be shown to the user 170 on a display or may be provided via an audio notification.

At 650, the controller processor 410 can indicate that electrode(s) at the stimulation unit 110 are not properly positioned and can further indicate that the electrode(s) require adjustment. The controller processor 410 can trigger an error signal to the user 170. The error signal may indicate that there is operation error at the stimulation unit 110, such as a short circuit, an open circuit, or defective electrodes. The error signal may be an error message shown to the user 170 on a display or an audio notification.

In some embodiments, in response to determining that the electrodes require adjustment, the controller processor 410 can generate guidance signals for further assisting with the positioning of the electrodes at the stimulation unit 110. The guidance signals may include at least one of an audio signal and visual illustrations. For example, a visual guide may be provided on a screen for illustrating how to properly position the electrodes.

After the electrodes at the stimulation unit 110 are properly positioned on the user 170, the controller unit 130 can continue to facilitate movement by the user 170. For example, when the FES system 102 is in the walking mode, the controller unit 130 can monitor the movement of the user 170 and determine if any changes in the stimulation signal is necessary for assisting with the gait of the user 170.

Figure 7:
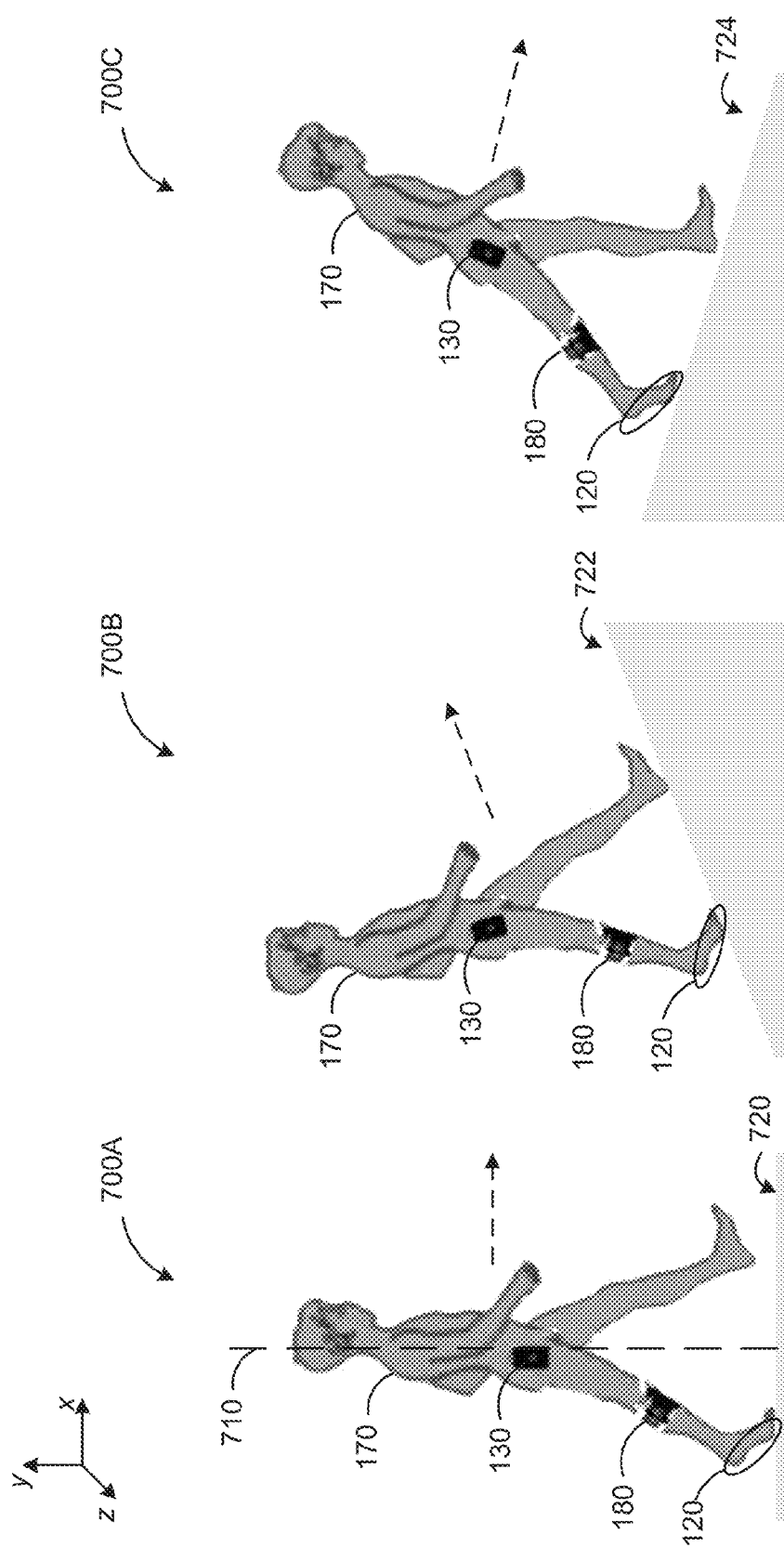
FIGS. 7A to 7C illustrate a user moving in different terrains.
Figure 8:
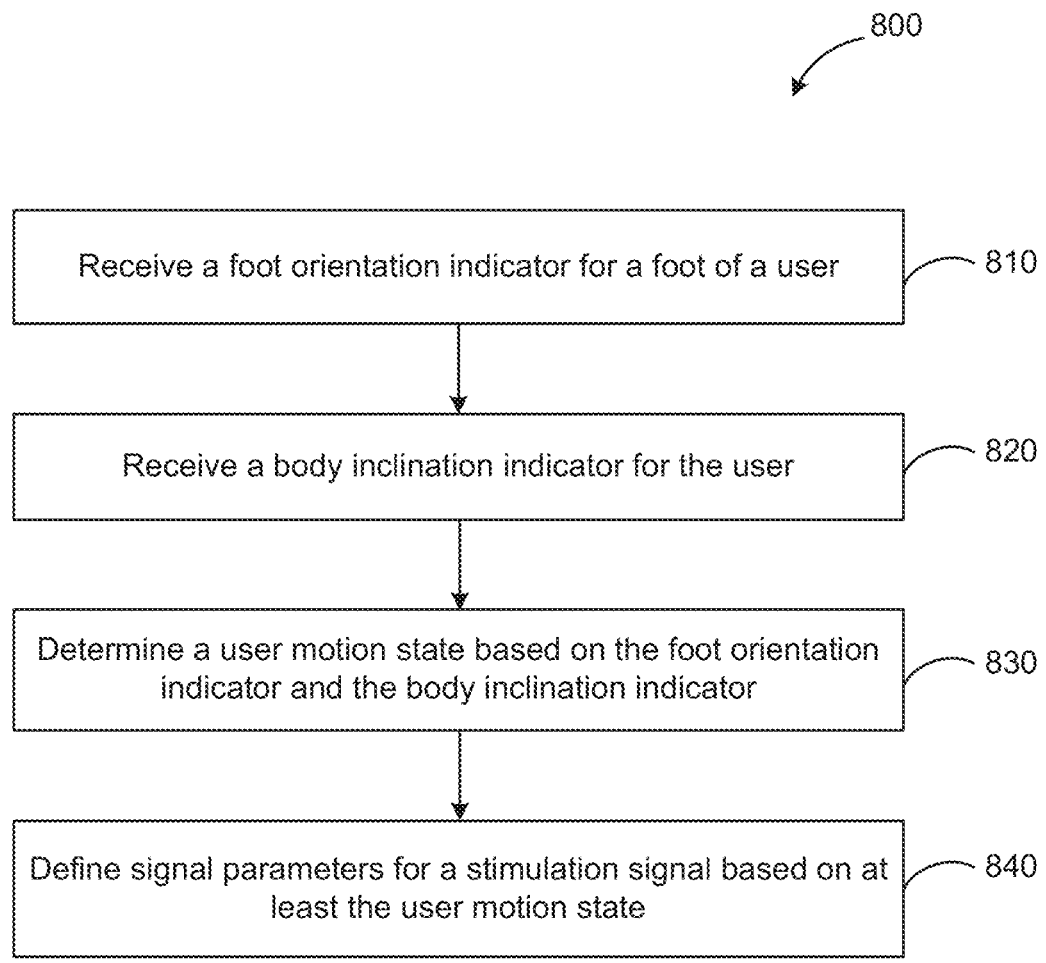
FIG. 8 is a flowchart of an example embodiment of a method of facilitating a gait of the user in accordance with the teachings herein.

An example embodiment of a method of facilitating the gait of the user 170 is described with simultaneous reference to FIGS. 7A to 7C and 8. FIGS. 7A to 7C illustrate the user 170 moving in different terrains. FIG. 8 is a flowchart of an example embodiment of a method 800 of facilitating the gait of the user 170 with the FES system 102.

As shown in each of FIGS. 7A to 7C, the stimulation unit 110 is provided along with a cuff 180 and the cuff 180 is located at a lower leg portion of the user 170. The sensor unit 120 is located at the foot of the user 170. As described, the sensor unit 120 can be located at the footwear worn by the user 170, such as being embedded in the insole of the footwear, for example. In this example embodiment, the sensor unit 120 is provided at the foot of the leg on which the cuff 180 is also worn. However, in other embodiments, the sensor unit 120 and the cuff 180 may be worn on different legs of the user 170 as long as the sensor unit 120 is located at the leg with the affected muscles. In some embodiments, a sensor unit 120 may be provided at each foot so that additional movement information may be collected. The controller unit 130 in FIG. 7A is carried by the user 170 near a waist area. In some other embodiments, the controller unit 130 can be located at areas other than the waist area of the user 170.

At 810, the controller processor 410 receives a foot orientation indicator for the foot of the user 170. The foot orientation indicator corresponds to an angular position of the foot relative to a reference axis, such as reference axis 710 shown in FIG. 7A. The reference axis 710 can be a longitudinal axis of the user 170 at an initial state. The initial state may correspond to a state of the user 170 as the user 170 first begins to move while wearing the FES system 102. For example, as illustrated in FIGS. 7A and 7B, the user 170 is moving along a substantially planar terrain 720 at 700A but then moves up an ascending terrain 722 at 700B. The initial state of user 170 can be the state of user 170 as shown at 700A and so the reference axis 710 corresponds to a y-axis of a Cartesian coordinate system.

The reference axis 710 can be updated by the user 170, such as when the controller processor 410 receives a reset signal from the user 170 via the user interface module 420, or can be updated each time the FES system 102 is powered on. For ease of exposition, the reference axis 710 shown in FIG. 7A also applies to each of FIGS. 7B and 7C.

The controller processor 410 receives the angular position of the foot from the sensor unit 120. While the user 170 is in the initial state, the angular position of the foot can be generally perpendicular to the reference axis 710 when the foot is not in motion. However, as the user 170 moves through different terrains, the angular position of the foot changes. FIG. 7B, for instance, illustrates the user 170 moving up the ascending terrain 722. The angular position of the foot is therefore oriented upwards with respect to the reference axis 710. FIG. 7C, on the other hand, illustrates the user 170 moving down a descending terrain 724 at 700C and therefore, the corresponding angular position of the foot is oriented downwards with respect to the reference axis 710.

At 820, the controller processor 410 receives a body inclination indicator for the user 170. Similar to the foot orientation indicator, the body inclination indicator also corresponds to a body position relative to the reference axis 710. The controller processor 410 can use the body inclination indicator to help distinguish between different motion states, as will be described. The body inclination indicator may be provided by an appropriate sensor(s) in the sensor module 470 of the controller unit 130, such as one or more gyroscope(s) for example.

The body inclination indicator of the user 170 at 700A is 0° relative to the reference axis 710 since the user 170 is moving along the substantially planar terrain 720. The body inclination indicators of user 170 at 700B and 700C, are different than 0° since the position of the user 170 varies away from the reference axis 710. In FIG. 7B, the body inclination indicator varies away from the reference axis 710 in the negative x-axis direction since the user 170 is moving up the ascending terrain 722 and therefore, the body of the user 170 is leaning backwards away from the reference axis 710. In FIG. 7O, the body inclination indicator also varies away from the reference axis 710 but in the positive x-axis direction since the user 170 is moving down the descending terrain 724. The body of the user 170, therefore, is leaning forwards away from the reference axis 710.

At 830, the controller processor 410 determines a motion state based on the foot orientation indicator and the body inclination indicator. The motion state can indicate a movement status of the user 170. For example, the motion state can be one of a fallen state, an active state and a stationary state.

The fallen state generally indicates that the user 170 fell or experienced a drop, the active state generally indicates that the user 170 is currently moving, and the stationary state generally indicates that the user 170 is currently not moving. When the user 170 is in the active state, the controller processor 410 can further determine whether the user 170 is experiencing a terrain change, such as from the substantially planar terrain 720 to the ascending terrain 722, for example.

Figure 9:
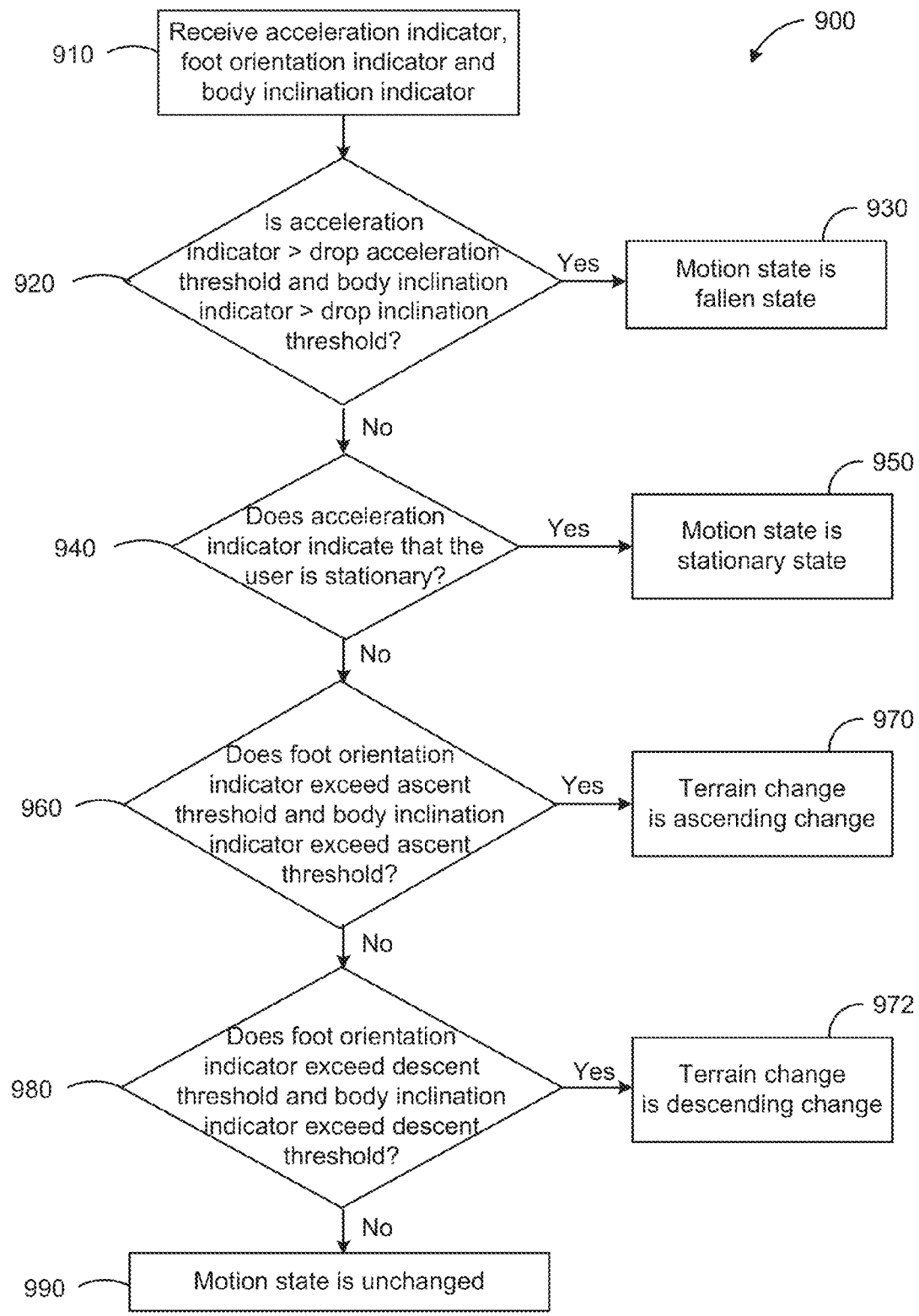
FIG. 9 is a flowchart of an example embodiment of a method for determining a motion state in accordance with the teachings herein.

Reference is now made to FIG. 9, which illustrates a flowchart of an example embodiment of a method 900 of determining the motion state.

At 910, the controller processor 410 receives an acceleration indicator, the foot orientation indicator, and the body inclination indicator for the user 170. The controller processor may receive the acceleration indicator from at least one of the sensor unit 120 and the sensor module 470. As described, the acceleration indicator can provide a rate at which a velocity of the user 170 changes with time. The acceleration indicator can be associated with the foot of the user 170 or another body part.

At 920, the controller processor 410 determines whether the acceleration indicator and the body inclination indicator exceed a drop threshold. The drop threshold includes one or more values or a range of values used by the controller processor 410 to determine if the user 170 is in the fallen state. The drop threshold can include, at least, a drop acceleration threshold and a drop inclination threshold. If the controller processor 410 determines that the acceleration indicator associated with the user 170 exceeds the drop acceleration threshold and that the body inclination indicator exceeds the drop inclination threshold, the controller processor 410 proceeds to 930. If not, the controller processor 410 proceeds to 940.

The drop acceleration threshold may be predetermined by the manufacturer or selected by a third party, such as a doctor or clinician, for the user 170. For an average user, the drop acceleration threshold may be within a range of approximately 1.5 g to 2.5 g. In some embodiments, the drop acceleration threshold may be approximately 1.8 g. The drop acceleration threshold may be stored at the storage module 440.

Similar to the drop acceleration threshold, the drop inclination threshold may also be predetermined by the manufacturer or selected by the third party for the user 170. For an average user, the drop inclination threshold may be within a range of approximately 30 to 60 degrees. In some embodiments, the drop inclination threshold may be 45 degrees. The drop inclination threshold may be stored at the storage module 440.

The body inclination indicator can be compared with the drop inclination threshold to determine whether the user 170 is leaning away from the reference axis 710 beyond a reasonable range. The body inclination indicator prevents the controller processor 410 for misidentifying a fallen state caused by significant changes in the acceleration of the user 170, such as when the user 170 is in a moving elevator.

At 930, the controller processor 410 determines the motion state is the fallen state. When the controller processor 410 determines that the acceleration indicator exceeds the drop acceleration threshold and the body inclination indicator exceeds the drop inclination threshold, the controller processor 410 can indicate that user 170 fell or dropped.

At 940, the controller processor 410 determines whether the acceleration indicator indicates the user 170 is stationary. The controller processor 410 can determine that the user 170 is stationary if the rate at which the velocity of the user 170 changes with time does not exceed 0 or if the nominal gravitational acceleration value provided in the acceleration indicator does not exceed 1 g. If the controller processor 410 determines that the acceleration indicator indicates that the user 170 is stationary, the controller processor 410 proceeds to 950. However, if the controller processor 410 determines that the acceleration indicator indicates that the user 170 is not stationary, the controller processor 410 can determine that the motion state is the active state.

At 950, the controller processor 410 determines the motion state is the stationary state. When the controller processor 410 determines that the acceleration indicator indicates that the user 170 is stationary, the controller processor 410 can indicate that user 170 is not in motion.

In some embodiments, the controller processor 410 can trigger one or more components of the FES system 102 to enter a low power state in response to detecting that the user 170 is in the stationary state. In some embodiments, the controller processor 410 may only trigger the low power state when the user 170 has been in the stationary state for at least a pre-determined duration of time.

In some embodiments, the controller processor 410 can further determine, at 960 and 980, whether there is a terrain change in the environment of the user 170. Therefore, there can be embodiments in which the method stops at 950, for example, in cases where the user 170 is not yet well enough to walk up an inclining slope or down a declining slope.

At 960, the controller processor 410 determines whether each of the foot orientation indicator and the body inclination indicator exceeds the ascent threshold.

The ascent threshold can include an angular value or a range of angular values. The ascent threshold may be predetermined by the manufacturer, selected by a third party, such as a doctor or clinician, for the user 170, or selected by the user 170. In some embodiments, the ascent threshold is within a range of approximately 15 to 25 degrees in a backward direction relative to the reference axis, or in the negative x-axis direction in the example of FIG. 7A since the reference axis 710 is the y-axis. The ascent threshold may be stored at storage module 440.

When the controller processor 410 determines that each of the foot orientation indicator and the body inclination indicator exceeds the ascent threshold, the controller processor 410 determines that there is a terrain change and that the terrain change is an ascending change (at 970). FIG. 7B shows an example of when the ascending change occurs. However, if the controller processor 410 determines that each of the foot orientation indicator and the body inclination indicator do not exceed the ascent threshold, the controller processor 410 proceeds to 980.

When the terrain change is the ascending change, the user 170 may require further assistance from the FES system 102. To facilitate the gait of the user 170, the controller processor 410 can define signal parameters that increase the intensity of the existing stimulation signal. In the case of foot drop, for example, increased intensity in the stimulation signals applied to the user 170 can further enhanced ankle dorsiflexion so that the user 170 can adapt to the ascending terrain 722 more easily.

At 980, the controller processor 410 determines whether each of the foot orientation indicator and the body inclination indicator exceeds a descent threshold.

Similar to the ascent threshold, the descent threshold can include an angular value or a range of angular values. The descent threshold may be predetermined by the manufacturer, selected by a third party, such as a doctor or clinician, for the user 170, or selected by the user 170. In some embodiments, the descent threshold is within a range of approximately 15 to 25 degrees in a forward direction relative to the reference axis 710, or in the positive x-axis direction in the example of FIG. 7A since the reference axis 710 is the y-axis. The descent threshold may be stored at storage module 440.

When the controller processor 410 determines that each of the foot orientation indicator and the body inclination indicator exceeds the descent threshold, the controller processor 410 determines that there is a terrain change and that the terrain change is a descending change (at 972). FIG. 7C shows an example of when there is a descending change. However, if the controller processor 410 determines that each of the foot orientation indicator and the body inclination indicator do not exceed the descent threshold, the controller processor 410 can determine that the motion state has not changed (at 990).

When the terrain change is the descending change, the user 170 may not require as much assistance from the FES system 102. Accordingly, the controller processor 410 can define signal parameters that decrease the intensity of the existing stimulation signal. In the case of foot drop, for example, movement on the descending terrain 724 likely requires less ankle dorsiflexion than when the user 170 moves along the substantially planar terrain 720 or the ascending terrain 722. Decreasing the intensity of the stimulation signal can help conserve power consumption and can also prevent unnecessary muscle strain in the user 170.

Referring again to FIG. 8, at 840, the controller processor 410 defines signal parameters for the stimulation signal based on at least the motion state of the user 170. The stimulation signal can be applied to the user 170 for facilitating the gait of the user 170. As will be described, the signal parameters corresponding to the stimulation signal can be varied by the controller processor 410 in order to help the user 170 adapt to different motion states and terrain changes that were just determined. For example, the controller processor 410 may continuously monitor the motion state and update the signal parameters accordingly. In some embodiments, a feedback condition signal may be provided to the controller processor 410 for indicating whether further adjustment to the signal parameters is required.

When the user 170 is in the fallen state, the controller processor 410 can define the signal parameters such that the corresponding stimulation signal includes at least one of generating an end signal for terminating any existing stimulation signals, turning off the FES system 102, transmitting the motion state to the external system 140, transmitting an emergency message to the external system 140 and generating an alarm signal. The emergency message may include a current location of the user 170 that may be provided by the communication module 430 (e.g., from the GPS receiver).

The end signal may, in some embodiments, always be generated when the controller processor 410 determines the user 170 is in the fallen state. The end signal terminates any further application of the stimulation signals to the user 170. The end signal may be particularly important in preventing injuries that may be caused by further application of the stimulation signals to the user 170 when the user 170 has fallen. The end signal can also help conserve power in the FES system 102 by preventing unnecessary generation of the stimulation signals at the stimulation unit 110, for example.

Transmission of the motion state to the external system 140 when the user 170 is in the fallen state can trigger response or assistance from third parties. For example, in response to receiving the fallen state, the external system 140 can trigger a notification to be sent to the third party, such as medical professional or emergency response personnel. The third party can contact the user 170 and, if necessary, send emergency response personnel to assist the user 170.

The alarm signal that can be generated based on the signal parameters defined by the controller processor 410 can be audio or visual.

When the user 170 is in the active state, the controller processor 410 can define the signal parameters based on at least the terrain change. As described, the controller processor 410 can define the signal parameters to increase the intensity (or amplitude) of the stimulation signal when the terrain change is the ascending change and to decrease the intensity of the stimulation signal when the terrain change is the descending change. In some embodiments, the signal parameters may be defined so that the corresponding stimulation signal is adjusted by one or more predetermined intervals.

In some further embodiments, the controller processor 410 can define the signal parameters to vary other aspects of the stimulation signal, such as a frequency of the stimulation signal, duration or width of a stimulation signal and other characteristics of the stimulation signal. The various characteristics may be used to elicit different effects on the user 170.

Figure 10A:
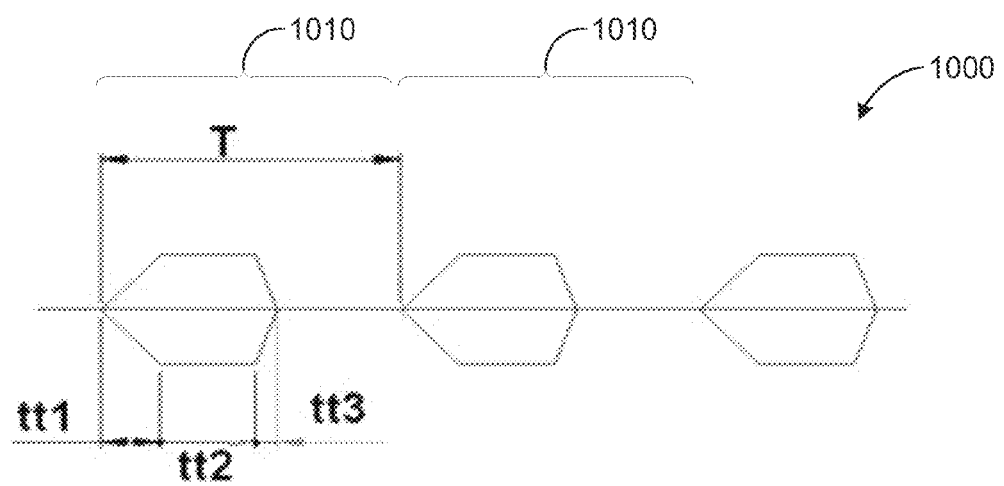
FIGS. 10A and 10B are example embodiments of a stimulation signal generated by the FES system.
Figure 10B:
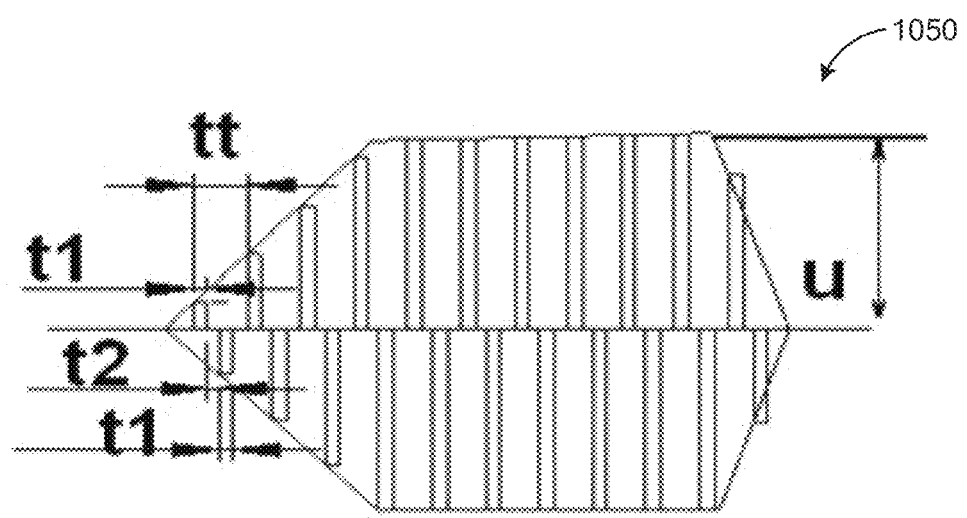

Reference is now made to FIGS. 10A and 10B, which illustrate example stimulation signals generated by the stimulation unit 110. As shown in FIG. 10A, a series 1000 of stimulation signal envelopes 1010 can be generated. Each stimulation signal envelope 1010 can be characterized with a stimulation cycle having a stimulation time T with a stimulation period during which one or more stimulation pulses may be applied to the user 170 and a rest period during which no stimulation pulses are applied to the user 170. The stimulation period can include a rising time tt1, a stimulation duration tt2 and a falling time tt3. Each of the stimulation time T, the rising time tt1, the stimulation duration tt2 and the falling time tt3 may be defined by the controller processor 410.

The stimulation signal 1050 illustrates the one or more pulses that may be applied to the user 170 during the stimulation period. Each pulse can be associated with a pulse time t1. The pulses may include positive pulses and negative pulses. Each positive pulse can be separated from a following negative pulse by a pulse separation interval t2. Two sequential positive pulses can be separated by a positive pulse separation interval tt. An amplitude u of the pulses during the stimulation duration tt2 generally corresponds to an intensity of the stimulation signal. Each of the pulse time t1, the pulse separation interval t2, the positive pulse separation interval tt, and the amplitude u may be defined by the controller processor 410.

For example, the frequency that is selected for the stimulation signal 1050 is a frequency of the gait of the user 170. The frequency can correspond to the stimulation time, tt, or the pulse separation interval t2. As shown in Table 1, different ranges of frequency in the stimulation signal 1050 may cause different effects on the muscles and nerves of the user 170.

TABLE 1

Example Frequency Ranges for the Stimulation Signal

| Frequency Range of Stimulation Signal | Effect of Stimulation |
| --- | --- |
| 1 to 3 Hz | Spasm reduction and relaxation |
| 7 to 9 Hz | Increase blood flow |
| 10 to 20 Hz | Endurance |
| 20 to 50 Hz | Neuromuscular stimulation |
| 50 to 70 Hz | Resistance training and muscle hypertrophy |
| 70 to 100 Hz | Increase muscle strength |
| 101 to 120 Hz | Explosive muscle strength |

It will be understood that other frequency ranges may be used and other effects may result.

In some embodiments, the frequency range of 20 to 50 Hz may be appropriate for the stimulation signal 1050 for facilitating the user 170 to adapt to different terrains. In some embodiments, the frequency range of 70 to 100 Hz may be appropriate for the stimulation signal 1050 for facilitating the user 170 to adapt to different terrains.

Generally, the values of the intensity and the duration of the stimulation signal 1050 need to be sufficient to at least stimulate the muscle or nerves. The intensity, as described, can correspond to the amplitude u of the pulses during the stimulation duration tt2 and the duration of the stimulation signal 1050 may correspond to the stimulation time t1, for example. The duration tt2 of the stimulation signal 1050, for example, may typically be within a range of 50 to 800 µs. For duration values that are lower, the controller processor 410 may define higher intensity values for the stimulation signal in order to obtain the desired result on the muscles or nerves of the user 170 that are being stimulated.

It will be further understood that each of the described characteristics of the stimulation signal 1050 may not be linearly related to the effects on the muscles or nerves. Instead, the controller processor 410 may vary multiple characteristics of the stimulation signal 1050 in order to cause a desired stimulation of the muscle or nerves. For example, the controller processor 410 may increase the amplitude u of the stimulation signal 1050 or increase the duration t1 of the stimulation signal 1050.

In some embodiments, each of the ascent threshold and the descent threshold may include multiple threshold levels. Each threshold level may correspond to a variation in an aspect of the stimulation signal 1050, such as the intensity, the frequency, and the duration. For example, the ascent threshold can include three different ascent threshold levels. A first ascent threshold level can correspond to a first variation level, a second ascent threshold level can correspond to a second variation level, and a third ascent threshold level can correspond to a third variation level. The first variation level may include increasing the intensity to a first intensity level for a first duration, the second variation level may include further increasing the intensity to a second intensity level that is higher than the first intensity level for a second duration that is longer than the first duration, and the third variation level may include increasing the intensity to a third intensity level at a higher frequency. When the controller processor 410 determines that each of the foot orientation indicator and the body inclination indicator exceeds only the first ascent threshold level, the controller processor 410 defines the signal parameters in accordance with the first variation level. The controller processor 410 can continue to monitor for further changes in the foot orientation indicator and the body inclination indicator, and to adjust the signal parameters based on the corresponding variation levels.

The threshold levels may be predefined or may vary based on the operation of the FES system 102. The predefined threshold levels may be stored at the storage module 440. In some embodiments, the threshold levels may vary based on data previously collected by the sensor module 470 and data received via the communication module 430. For example, the controller processor 410 may lower an ascent threshold level if the controller processor 410 determines, based on previously defined signal parameters that the user 170 requires significant assistance from the FES system 102 for the current gait. In that case, the controller processor 410 can determine that the user 170 is having difficulty navigating the terrain and the controller processor 410 can adapt the FES system 102 to the terrain by making the controller unit 130 more sensitive to smaller changes in the terrain.

Each variation level may, in some embodiments, correspond to a predefined set of signal parameters or predefined change to the signal parameters. For example, if the variation level corresponds to a predefined set of signal parameters, the controller processor 410 can define the signal parameters to correspond to predefined signal parameters associated with the corresponding variation level. On the other hand, if the variation level corresponds to predefined change to the signal parameters, the controller processor 410 can define the signal parameters by increasing or decreasing the existing signal parameters by the predefined change.

Various embodiments of systems, device and methods that can be used to facilitate the gait of a user have been described here by way of example only. Various modifications and variations may be made to these example embodiments without departing from the spirit and scope of the embodiments, which is limited only by the appended claims. Also, in the various user interfaces illustrated in the figures, it will be understood that the illustrated user interface text and controls are provided as examples only and are not meant to be limiting. Other suitable user interface elements may be possible.

We claim:

1. A method of facilitating a gait of a user with a functional electrical stimulation (FES) orthotic system, wherein at a controller unit, the method comprises:
   receiving a foot orientation indicator for a foot of the user, the foot orientation indicator corresponding to an angular position of the foot relative to a reference axis, the reference axis being a longitudinal axis of the user in an initial state;
   receiving a body inclination indicator for the user, the body inclination indicator corresponding to a body position relative to the reference axis;
   receiving an acceleration indicator for the user;
   determining a motion state based on the foot orientation indicator and the body inclination indicator, the motion state indicating a movement status of the user;
   identifying the motion state is a fallen state when the acceleration indicator exceeds a drop acceleration threshold and the body inclination indicator exceeds a drop inclination threshold;
   identifying the motion state is an active state when the acceleration indicator indicates that the user is not stationary and is less than the drop acceleration threshold; and
   defining signal parameters for a stimulation signal based on at least the motion state, the stimulation signal being applied to the user for facilitating the gait of the user.

2. The method of claim 1, wherein, in response to determining the motion state is the fallen state, defining signal parameters further comprises generating an end signal for terminating any existing stimulation signal.

3. The method of claim 1, wherein, in response to determining the motion state is the fallen state, defining signal parameters for the stimulation signal further comprises at least one of:
   turning off the FES orthotic system;
   transmitting an emergency message to a remote system;
   transmitting the motion state to the remote system; and
   generating an alarm signal.

4. The method of claim 1, wherein the drop acceleration threshold is within a range of 1.5 g to 2.5 g.

5. The method of claim 1, wherein the drop inclination threshold is within a range of 30 to 60 degrees.

6. The method of claim 1, further comprising:
   in response to determining the motion state is the active state, determining a terrain change of an environment of the user based on the foot orientation indicator and the body inclination indicator.

7. The method of claim 6, wherein determining the terrain change comprises:
   identifying the terrain change is an ascending change when each of the foot orientation indicator and the body inclination indicator exceeds an ascent threshold; and
   identifying the terrain change is a descending change when each of the foot orientation indicator and the body inclination indicator exceeds a descent threshold.

8. The method of claim 7, wherein defining signal parameters for the stimulation signal further comprises varying at least one aspect of the stimulation signal.

9. The method of claim 8, wherein the at least one aspect of the stimulation signal comprises an intensity of the stimulation signal, a frequency of the stimulation signal and a duration of the stimulation signal.

10. The method of claim 9, wherein varying the at least one aspect of the stimulation signal comprises:
    increasing an intensity of the stimulation signal when the terrain change is the ascending change; and
    decreasing the intensity of the stimulation signal when the terrain change is the descending change.

11. The method of claim 7, wherein the ascent threshold is within a range of 15 to 25 degrees in a backward direction relative to the reference axis.

12. The method of claim 7, wherein the descent threshold is within a range of 15 to 25 degrees in a forward direction relative to the reference axis.

13. The method of claim 1, wherein the body inclination indicator is associated with a body part of the user other than the foot.

14. The method of claim 1, wherein defining signal parameters for the stimulation signal further comprises adjusting an aspect of the stimulation signal by a predetermined interval.

15. A functional electrical stimulation (FES) orthotic system for facilitating a gait of a user, the FES orthotic system comprising:
    a controller unit comprising a controller processor and at least one sensor, the controller processor configured to:
       receive a foot orientation indicator for a foot of the user, the foot orientation indicator corresponding to an angular position of the foot relative to a reference axis, the reference axis being a longitudinal axis of the user in an initial state;
       receive, from the at least one sensor, a body inclination indicator for the user, the body inclination indicator corresponding to a body position relative to the reference axis;
       receive, from the at least one sensor, an acceleration indicator for the user;
       determine a motion state based on the foot orientation indicator and the body inclination indicator, the motion state indicating a movement status of the user;
       identify the motion state is a fallen state when the acceleration indicator exceeds a drop acceleration threshold and the body inclination indicator exceeds a drop inclination threshold;
       identify the motion state is an active state when the acceleration indicator indicates that the user is not stationary and is less than the drop acceleration threshold; and define signal parameters for a stimulation signal based on at least the motion state, the stimulation signal being applied to the user to facilitate the gait of the user.

16. The FES system of claim 15, wherein, in response to the controller processor determining the motion state is the fallen state, the controller processor is further configured to generate an end signal for terminating any existing stimulation signal.

17. The FES system of claim 15, wherein, in response to the controller processor determining the motion state is the fallen state, the controller processor is further configured to perform at least one of:
turning off the FES system;
transmitting an emergency message to a remote system;
transmitting the motion state to the remote system; and
generating an alarm signal.

18. The FES system of claim 15, wherein the drop acceleration threshold is within a range of 1.5 g to 2.5 g.

19. The FES system of claim 15, wherein the drop inclination threshold is within a range of 30 to 60 degrees.

20. The FES system of claim 15, wherein, in response to the controller processor determining the motion state is the active state, the controller processor is further configured to:
determine a terrain change of an environment of the user based on the foot orientation indicator and the body inclination indicator.

21. The FES system of claim 20, wherein the controller processor is further configured to:
identify the terrain change is an ascending change when each of the foot orientation indicator and the body inclination indicator exceeds an ascent threshold; and
identify the terrain change is a descending change when each of the foot orientation indicator and the body inclination indicator exceeds a descent threshold.

22. The FES system of claim 21, wherein the controller processor is further configured to vary at least one aspect of the stimulation signal.

23. The FES system of claim 22, wherein the at least one aspect of the stimulation signal comprises an intensity of the stimulation signal, a frequency of the stimulation signal and a duration of the stimulation signal.

24. The FES system of claim 22, wherein the controller processor is further configured to:
increase an intensity of the stimulation signal when the terrain change is the ascending change; and
decrease the intensity of the stimulation signal when the terrain change is the descending change.

25. The FES system of claim 21, wherein the ascent threshold is within a range of 15 to 25 degrees in a backward direction relative to the reference axis.

26. The FES system of claim 21, wherein the descent threshold is within a range of 15 to 25 degrees in a forward direction relative to the reference axis.

27. The FES system of claim 15, wherein the body inclination indicator is associated with a body part of the user other than the foot.

28. The FES system of claim 15, wherein the controller processor is further configured to adjust an aspect of the stimulation signal by a predetermined interval.

29. A non-transitory computer readable medium comprising a plurality of instructions executable on a processor of a device for adapting the processor to implement a method of facilitating a gait of a user with a functional electrical stimulation (FES) orthotic system, wherein the instructions comprise, at the device:
receiving a foot orientation indicator for a foot of the user, the foot orientation indicator corresponding to an angular position of the foot relative to a reference axis, the reference axis being a longitudinal axis of the user in an initial state;
receiving a body inclination indicator for the user, the body inclination indicator corresponding to a body position relative to the reference axis;
receiving an acceleration indicator for the user;
determining a motion state based on the foot orientation indicator and the body inclination indicator, the motion state indicating a movement status of the user;
identifying the motion state is a fallen state when the acceleration indicator exceeds a drop acceleration threshold and the body inclination indicator exceeds a drop inclination threshold;
identifying the motion state is an active state when the acceleration indicator indicates that the user is not stationary and is less than the drop acceleration threshold; and
defining signal parameters for a stimulation signal based on at least the motion state, the stimulation signal being applied to the user for facilitating the gait of the user.

* * * * *